(12) United States Patent
Peng et al.

(10) Patent No.: US 8,734,580 B2
(45) Date of Patent: May 27, 2014

(54) CARBONYL PROPYL SULFURYL ANTHRAPYRIDONE SULFONIC ACID COMPOUNDS AND THEIR PREPARATION METHODS AND APPLICATIONS

(71) Applicants: Dalian University of Technology, Dalian (CN); Zhuhai Ninestar Management, Co., Ltd., Zhuhai (CN)

(72) Inventors: Xiaojun Peng, Dalian (CN); Jinhe Wu, Dalian (CN); Zhi Long, Dalian (CN); Rong Zhang, Dalian (CN); Licheng Liaoning, Dalian (CN); Feng Wang, Zhuhai (CN); Shaolei Li, Zhuhai (CN); Jiangli Fan, Dalian (CN); Fengling Song, Dalian (CN); Shiguo Sun, Dalian (CN)

(73) Assignees: Dalian University of Technology, Dalian (CN); Zhuhai Ninestar Management Co., Ltd., Zhuhai (CN)

( * ) Notice: Subject to any disclaimer, the term of this patent is extended or adjusted under 35 U.S.C. 154(b) by 0 days.

(21) Appl. No.: 13/919,996

(22) Filed: Jun. 17, 2013

(65) Prior Publication Data
US 2013/0276667 A1    Oct. 24, 2013

Related U.S. Application Data

(63) Continuation of application No. PCT/CN2011/079228, filed on Sep. 1, 2011.

(51) Int. Cl.
C09D 11/02 (2006.01)
C07D 221/18 (2006.01)

(52) U.S. Cl.
USPC .................. 106/31.47; 546/76

(58) Field of Classification Search
USPC .................. 106/31.47; 546/76
See application file for complete search history.

(56) References Cited

U.S. PATENT DOCUMENTS

| | | | |
|---|---|---|---|
| 3,517,013 A | 6/1970 | Akamatsu et al. | 260/278 |
| 4,902,798 A * | 2/1990 | Nakamatsu et al. | 546/76 |
| 5,367,075 A * | 11/1994 | Nakamatsu et al. | 546/76 |
| 6,183,549 B1 | 2/2001 | Wight | 106/31.51 |
| 6,460,988 B1 * | 10/2002 | Mafune et al. | 106/31.47 |
| 6,471,760 B1 | 10/2002 | Matsumoto et al. | 106/31.47 |
| 6,648,952 B1 | 11/2003 | Matsumoto et al. | 106/31.47 |
| 7,785,411 B2 * | 8/2010 | Ishii et al. | 106/31.47 |
| 7,828,886 B2 * | 11/2010 | Baettig et al. | 106/31.47 |
| 7,871,464 B2 * | 1/2011 | Ono et al. | 106/31.47 |
| 7,985,287 B2 * | 7/2011 | Murakami et al. | 106/31.47 |
| 2002/0036681 A1 | 3/2002 | Mafune et al. | 347/100 |
| 2002/0041318 A1 | 4/2002 | Osumi et al. | 347/100 |
| 2004/0134383 A1 | 7/2004 | Matsumoto et al. | 106/31.47 |
| 2005/0057607 A1 | 3/2005 | Tomioka et al. | 347/43 |
| 2005/0115458 A1 | 6/2005 | Oki et al. | 106/31.47 |
| 2005/0115459 A1 | 6/2005 | Hanmura et al. | 106/31.47 |
| 2006/0219131 A1 | 10/2006 | Matsumoto et al. | 106/31.47 |
| 2007/0242100 A1 | 10/2007 | Takuhara et al. | 347/43 |
| 2007/0263055 A1 | 11/2007 | Kitamura et al. | 347/100 |
| 2008/0257209 A1 | 10/2008 | Kitamura et al. | 106/31.48 |
| 2010/0015410 A1 | 1/2010 | Matsumoto et al. | 428/195.1 |
| 2010/0075047 A1 | 3/2010 | Baettig et al. | 427/256 |
| 2010/0080908 A1 | 4/2010 | Wachi et al. | 427/256 |

FOREIGN PATENT DOCUMENTS

| | | |
|---|---|---|
| CN | 101298526 A | 11/2008 |
| CN | 101370882 A | 2/2009 |

(Continued)

OTHER PUBLICATIONS

International Search Report of International Application No. PCT/CN2011/079228, dated Jun. 28, 2012.

Primary Examiner — Helene Klemanski
(74) Attorney, Agent, or Firm — J.C. Patents

(57) ABSTRACT

The present invention relates to compounds shown in the general formula (I) or (III), the salts thereof or their mixtures, as well as their preparation method and application. In the general formula (I), $X_1$ is H or $CO_2H$; $X_2$ is OH or phenyl group with 0-2 sulfonic acid substituents, and the sulfonic acid substituents are located at random positions of a benzene ring; when $X_2$ is OH, $X_1$ is H; when $X_2$ is phenyl group with 0-2 sulfonic acid substituents, $X_1$ is H or $CO_2H$; n is an integer of 0-2; and in the general formula (III), n and m are respectively an integer of 0-2. The compounds and the mixtures not only have improved light resistance, ozone resistance and water resistance, but also have excellent water solubility and long-term stability in ink-jet ink.

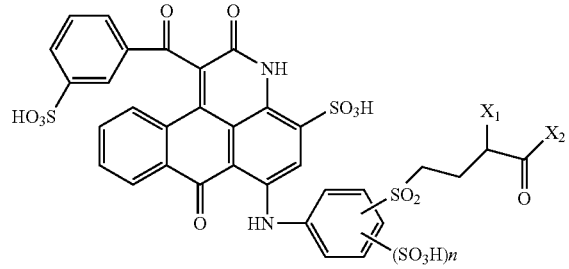

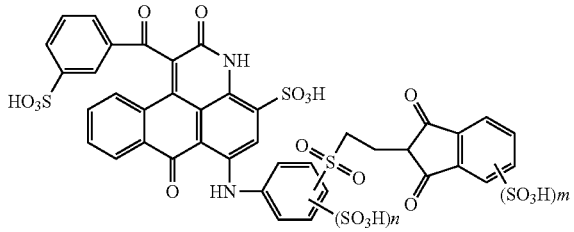

17 Claims, No Drawings

(56) References Cited

FOREIGN PATENT DOCUMENTS

| | | |
|---|---|---|
| CN | 101547976 A | 9/2009 |
| CN | 101848970 A | 9/2010 |
| CN | 101925658 A | 12/2010 |
| EP | 0 927 747 A1 | 7/1999 |
| EP | 1 626 070 A1 | 2/2006 |
| GB | 2 353 533 A | 2/2001 |
| GB | 2 464 188 A | 4/2010 |
| JP | 2000-109464 A | 4/2000 |
| JP | 2000-191660 A | 7/2000 |
| JP | 2002-069349 A | 3/2002 |
| JP | 2002-332419 A | 11/2002 |
| JP | 2006-010910 A | 1/2006 |
| JP | 2006-199922 A | 8/2006 |
| JP | 2007-138124 A | 6/2007 |
| JP | 2007-224119 A | 9/2007 |
| JP | 2012-041315 A | 3/2012 |
| WO | WO 2008/056699 A1 * | 5/2008 |
| WO | WO2009/044094 A2 | 4/2009 |
| WO | WO 2009/093433 A1 * | 7/2009 |
| WO | WO2009/116243 A1 | 9/2009 |

* cited by examiner

CARBONYL PROPYL SULFURYL ANTHRAPYRIDONE SULFONIC ACID COMPOUNDS AND THEIR PREPARATION METHODS AND APPLICATIONS

CROSS-REFERENCE TO RELATED APPLICATIONS

This application is a continuation of International Application No. PCT/CN2011/079228, filed on Sep. 1, 2011. The contents of the above identified applications are incorporated herein by reference in their entireties.

FIELD OF THE TECHNOLOGY

This invention relates to a class of novel anthrapyridone sulfonic acid compounds, their preparation methods and applications. It especially relates to anthrapyridone sulfonic acid compounds with carbonyl propyl sulfuryl, the salts thereof or their mixtures, as well as the applications as magenta colorant.

BACKGROUND

Among color recording methods, ink-jet printing is one of the typical ones. So far, varieties of ink jetting methods have been developed to form fine ink drops which will be adsorbed on recording materials (e.g., paper, film, fabric, etc.) to achieve the purpose of recording. As the nozzles do not contact the recording materials, so ink jet printers are characterized by quietness as well as ease in realizing miniaturization, high-speed and colorization. Therefore, ink jet printing has been developed rapidly in recent years.

Traditional inks are prepared as follows: water-soluble dyes are dissolved in aqueous medium and water-soluble organic solvents capable of preventing inks from blocking nibs are added to prepare inks for fountain pens and brush pens. Different from traditional inks, inkjet inks requires to be capable of forming high-density images, not blocking nozzles, drying well, bleeding little and being stored stably. In addition, images formed by ink-jet inks must have water resistance, light resistance, moisture resistance, ozone resistance, solubility, and fastness of these properties.

When applications of ink-jet printers expand from small printers to industrial large printers, higher requirements are raised for fastness of water resistance, moisture resistance, light resistance and gas resistance. Water resistance: Usually the substrate surface may adsorb porous silicon oxide, cationic polymers, alumina sol or special ceramics, and thus if dyes are applied on paper surface together with such organic or inorganic particles as well as PVA resin, water resistance can be significantly improved. Light resistance: In the four primary colors, namely yellow, magenta, cyan and black, magenta has the weakest light resistance and can seriously affect image quality; therefore, it has become an important subject to improve light resistance of magenta dyes. Moisture resistance: if printed images are to be saved in a high-humidity environment, it is required that dyes, as part of recording materials, are of good anti-bleeding fastness. If bleeding of dyes occurs, image quality will be significantly reduced, especially on occasions that high requirements are imposed on color matching for photos. However, compared with water resistance, improvement of light resistance, moisture resistance, ozone resistance and solubility are more difficult to be realized.

In addition, with the wide popularity of digital cameras in recent years, the opportunity to print photos at home is increasing. When the printed products are stored, oxidizing gases in indoor air which causes discoloration of images has also become one of the problems. Oxidizing gases cause discoloration and fading of images by reaction with the dyes on or in the recording paper. Particularly, ozone gas is a principal substance of promoting oxidization and fading of inkjet printed images, so the improvement of ozone gas resistance has become a subject equally important as the improvement of light resistance.

Typical examples of magenta dyes for inkjet inks include: xanthene type rhodamine dyes and azo dyes derived from H-acid coupling. While rhodamine dyes are most prominent in tone and brightness, they are extremely poor in light resistance. H-acid derived azo dyes are of good luster and water resistance and meanwhile are of poor light resistance, ozone resistance and brightness; particularly compared with cyan dyes with copper phthalocyanine as the representative and yellow azo dyes, it is still of poor light resistance.

In recent years, magenta dyes of outstanding light resistance have been developed, including anthrapyridone dyes. They have no Carbonyl Propyl Sulfuryl on their molecular scaffolds, indicating advantages of brightness, light resistance, ozone resistance, etc.

Examples include patents of Fuji Photo Film: JP2007138124A, JP2007224119A, CN101370882A, WO2009044094A2, US2010080908A1, GB2464188A; patents of Canon: US2002041318A1, US2002036681A1, JP2002069349A, JP2006199922A, CN101298526A, US2007242100A1, US2005057607A1; patents of Epson: US2005115458A1, US2005115459A1, US2007263055A1, US2008257209A1; patents of Avecia: U.S. Pat. NO. 6183549B1, and GB2353533A; Patents of Nippon Kayaku Co., Ltd.: EP0927747A1, JP2000109464A, JP2000191660A, U.S. Pat. No. 6471760B1, JP2002332419, U.S. Pat. No.6648952B1, US2004134383A1, EP1626070A1, US2006219131A1, WO2009116243A1, CN101547976A, US2010015410A1 (2010.1.21); patents of ILFORD: US2010075047A1 and the like.

However, dyes revealed in these patents do not meet all requirements of tone, brightness, light resistance, water resistance, ozone resistance as well as solubility and solution stability. Although light resistance and ozone resistance of some dyes have been improved, the solubility of the dyes and the long-term stability of inkjet inks are still insufficient. Long-term stability of dyes in inks is associated with their solubility; especially the solubility of dyes in water is not ideal on many occasions.

SUMMARY

To solve the mentioned problems, the inventor of the present invention found that the carbonyl propyl sulfuryl anthrapyridone sulfonic acid compounds shown in the general formula (I) or (III) in a form of free acid or salts thereof or a mixture of the compounds or a mixture of the salts of the compounds can solve the problems.

The purpose of the present invention is to provide a class of magenta dyes compounds and their mixture (accurately carbonyl propyl sulfuryl anthrapyridone sulfonic acid compounds, salts thereof or their mixtures) with improved light resistance, ozone resistance, water resistance as well as outstanding water solubility and long-term stability in inkjet inks.

The first aspect of the present invention relates to a class of compounds shown in general formula (I) or (III), salts thereof or their mixture.

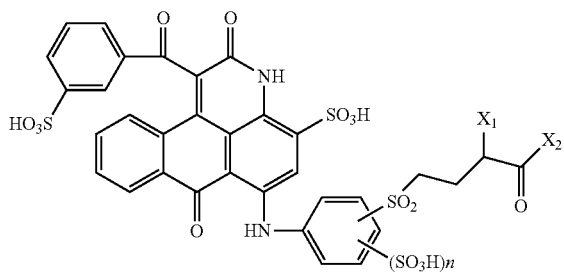

In the general formula (I):
X₁ is H or CO₂H;
X₂ is OH or phenyl group with 0-2 sulfonic acid substituents, and the sulfonic acid substituents are located at random positions of a benzene ring;
When X₂ is OH, X₁ is H;
When X₂ is phenyl group with 0-2 sulfonic acid substituents, X₁ is H or CO₂H;
n is an integer of 0-2;

In the general formula (III), n and m are respectively an integer of 0-2.
In a preferred embodiment, n and m are respectively an integer of 1-2.

In another preferred embodiment, salts of the compounds shown in the general formula (I) or (III) is selected from the following cation salts: Li⁺, Na⁺, K⁺, NH₄⁺, or organic ammonium salts N⁺R₁R₂R₃R₄, of which R₁, R₂, R₃, R₄ are respectively the same or different H, $C_{1-18}$ alkyl group, cyclohexyl group, CH₂CH₂OH, CH(CH₃)CH₂OH or benzyl group.

The second aspect of the present invention relates to a method for preparing the compounds shown in the general formula (I) or (III), the salts thereof or the mixture of the compounds, comprising the following steps:
(1) Synthesizing an intermediate compound shown in the general formula (V):

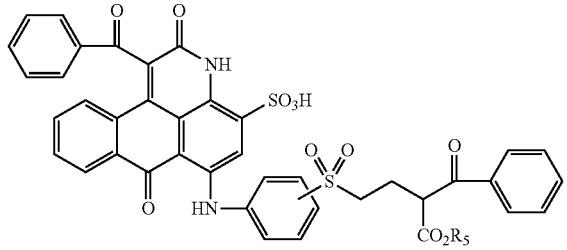

In the general formula (V), R₅ is $C_1$-$C_4$ alkyl group;
The synthesis steps comprise: based on a compound shown in the general formula (IV) or (IV') as a raw material, carrying out cyclization reaction on the compound shown in the general formula (IV) or (IV') and benzoyl acetic acid ester

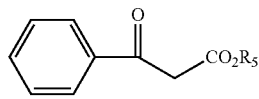

in an organic solvent at the temperature of 100-250° C. for 2-10 h to form the intermediate compound shown in the general formula (V),

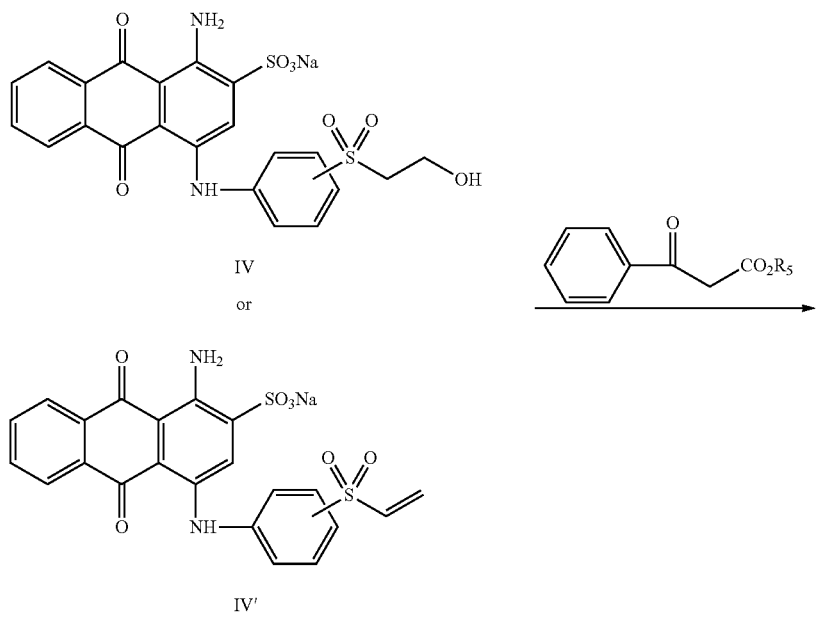

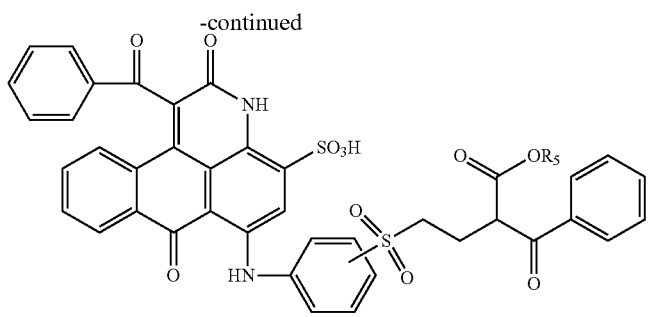

V

Cool the reaction system after the cyclization and filter the compound of general formula (V) separated out from the liquid reaction system to obtain the solid intermediate (V) compounds.

The reaction temperature is preferably 100-200° C., and more preferably 130-190° C.; and the reaction time is preferably 2-8 h, more preferably 2-5 h, and most preferably 2-4 h;

The aforesaid organic solvent has the boiling point of 100-300° C. and can dissolve or partially dissolve the reaction raw material (IV) or (IV'), and the boiling point is preferably 140-250° C., and more preferably 140-200° C.;

(2) Sulfonation and decomposition step: the intermediate compound shown in the general formula (V) is sulfonated with fuming sulfuric acid ($SO_3.H_2SO_4$) containing 5-30% $SO_3$ or chlorosulfonic acid under the temperature of 10-120° C., and simultaneously decomposition reaction occurs for 2-4 h, preferably 3-4 h to generate a mixture, wherein the mixture comprises one or more the compounds shown in the general formula (I) and one or more compounds shown in the general formula (III);

The sulfonation temperature is preferably 10-100° C., and the content of sulfur trioxide in fuming sulfuric acid is preferably 5-20%, and more preferably 6-15%;

(3) Salting-out step: the mixture obtained in the step (2) is salted out with a salt to generate a salt mixture, wherein the salt mixture comprises one or more salts of the compounds shown in the general formula (I), and one or more salts of the compounds shown in the general formula (III);

The salt used in the salting-out step is preferably an inorganic salt, and the inorganic salt is preferably selected from ammonium chloride, sodium chloride or lithium chloride;

(4) Separation step: the salts of the compounds shown in the general formula (I) and the general formula (III) are separated out from the salt mixture by adopting reversed phase ion-pair chromatography, and the obtained salts of the compounds are respectively desalinated to respectively generate the compounds shown in the general formula (I) and (III).

In a preferred embodiment, in the step (1), after the cyclization reaction is finished, the reaction system is cooled to 0-50° C., preferably 0-30° C.

In another preferred embodiment, in the step (1), the organic solvents used in the cyclization reaction include one or more of the followings: toluene, dimethylbenzene/isomers of xylene dimethylbenzene/isomer mixture, trimethylbenzene/isomers of trimethylbenzene/isomer mixture, diethylbenzene/isomers of diethylbenzene/isomer mixture, triethylbenzene/isomers of triethylbenzene/isomer mixture, petroleum ether, ethylene glycol dimethyl ether, ethylene glycol diethyl ether, ethylene glycol dipropyl ether, ethylene glycol dibutyl ether, 1,2-propylene glycol dimethyl ether, 1,2-propylene glycol diethyl ether, 1,2-propylene glycol dipropyl ether, 1,2-propylene glycol dibutyl ether, diethylene glycol dimethyl ether, diethylene glycol diethyl ether, diethylene glycol dipropyl ether, diethylene glycol dibutyl ether, chlorobenzene, dichlorobenzene/isomers of dichlorobenzene/isomer mixture, nitrobenzene, dimethyl sulfoxide (DMSO), dimethyl formamide (DMF), N-methyl pyrrolidone, sulfolane, and mixture of the above solvents.

Said organic solvents may preferably include: dimethylbenzene, diethylbenzene, trimethylbenzene, chlorobenzene, dichlorobenzene, nitrobenzene, DMSO, DMF, or their mixture.

In another preferred embodiment, in the step (1): during or after the reaction system cools down, add low-boiling point organic solvents with low solubility to the intermediate (V) and boiling points of 30-150° C. to promote full separation of the intermediate (V). The low-boiling point organic solvent is preferably selected from methanol, ethanol, propanol, isopropanol, acetone, acetonitrile, petroleum ether, cyclohexane, or their mixtures.

In another preferred embodiment, add alkalis to the cyclization reaction of step (1) to promote the reaction. Said alkalis may include one or more of the followings: sodium carbonate, sodium bicarbonate, potassium carbonate, potassium bicarbonate, lithium carbonate, lithium bicarbonate, ammonium carbonate, ammonium bicarbonate, sodium phosphate, disodium hydrogen phosphate, potassium phosphate, dipotassium hydrogen phosphate, ammonium phosphate, diammonium hydrogen phosphate, lithium phosphate, dilithium hydrogen phosphate, sodium acetate, potassium acetate, lithium acetate, ammonium acetate, sodium oxalate, potassium oxalate, lithium oxalate, ammonium oxalate, sodium hydroxide, potassium hydroxide, aluminum hydroxide or lithium hydroxide, and more preferably sodium carbonate and sodium bicarbonate The third aspect of the present invention relates to a type of ink containing the synthesized compound, salts thereof or their mixtures. Said ink is preferably printing ink, painting ink or inkjet ink; Said inkjet ink is preferably water-based or solvent-based or aqueous solvent-based inkjet ink.

The fourth aspect of the present invention relates to a composition of water-based inkjet ink consisting of 1-20% of the synthesized compounds, salts thereof or their mixture by weight, 5-50% of organic solvents miscible with water by weight, and 30-94% of water by weight based on the total weight of the compound, wherein the sum of the component contents is 100%.

Said water-miscible organic solvents may include one or more of the followings: ethanol, propanol, isopropanol, ethylene glycol, diethylene glycol, triethylene glycol, glycerol, ethylene glycol monobutyl ether, diethylene glycol monobutyl ether, triethylene glycol monobutyl ether, propylene glycol, butanediol, pentanediol, hexanediol, diglycerol, 2-pyrrolidone and N-methyl-2-pyrrolidone.

The fifth of the present invention relates to a coating (preferably outdoor coating), paint (preferably outdoor paint), laser printing toner or marker, comprising the synthesized compounds, salts thereof or their mixtures.

The sixth aspect of the present invention relates to an application of the synthesized compounds, salts thereof or their mixture, serving as a coloring agent for the following materials: ink, coating, paint, laser printing toner, marker, fabric (preferably woven fabrics, knitted fabrics or non-woven fabrics), glass, ceramics or polymers (preferably rubber, plastic or fiber).

The compounds and their mixture provided by the invention have the following beneficial effects:
1) Compounds and salts thereof in general formula (I) and (III) have such structural characteristics: carbonyl propyl sulfuryl is introduced to the sulfonic acid compounds of substituted anthrapyridone to increases the water-solubility of dyes;
2) The introduction of carbonyl propyl sulfuryl reduces the electron cloud density of parent dye molecules and further improves the light resistance and ozone resistance;
3) The introduction of carbonyl propyl sulfuryl enhances the flexibility of the dye molecule, which makes the dye not easy to crystallize. The affinity with an organic humectant such as ethylene glycol and glycerol additive in the ink is increased, and the ink stability is favorably improved.
4) In the preparation methods described in the present invention, commercially available blue dye derivatives are used as basic raw materials for synthesis, which is thus characterized by convenience in operation and low costs. The currently available patent techniques take non-dye compounds as the starting materials, which require higher costs and more reaction steps.

The introduced carbonyl propyl sulfuryl group contains a water-soluble group, which can not only reduces the electron cloud density of molecules and improves photooxidation resistance and ozone resistance of compounds, but also improves the solubility of dyes and molecular flexibility as well as the long-term stability of dyes in inks;

In the preparation methods described in the present invention, industrially and massively produced dyes are used as starting materials, which may shorten the preparation process and reduce the cost.

The compounds and the mixture thereof in this invention are applicable to be used as a colorant in multiple materials, such as ink, coating, paint, laser printing toner, marker, paper, fabric, glass, ceramic, or polymeric material.

Dye compounds and their mixture of the present invention are prominent in water solubility and long-term stability, which are particularly suitable for the luster and brightness requirements for inkjet printing. The fastness of light resistance, moisture resistance and ozone resistance of images printed with inkjet inks prepared by the involved dye compounds is outstanding, and high brightness tone can be achieved on inkjet recording materials.

DETAILED DESCRIPTION

The mixture provided by the present invention refers to: mixture of the compounds shown in the general formula (I), mixture of the compounds shown in the general formula (III), mixture of the compounds shown in the general formula (I) and (III), mixture of the salts of the compounds shown in the general formula (I), mixture of the salts of the compounds shown in the general formula (III), and mixture of the salts of the compounds shown in the general formula (I) and (III). In the said mixtures, the compounds or the salts thereof can be mixed at a random ratio.

In practical application, the salt form of the carbonyl propyl sulfuryl anthrapyridone sulfonic acid compounds shown in the general formula (I) and (III) is generally used. The invention relates to the compounds, salts thereof or their mixtures, preferably the mixture form of the salts of the compounds.

The applications of these compounds, salts thereof or their mixtures are characterized by brightness and extremely light tones on inkjet recording paper, outstanding water solubility and good filterability on the filter membrane. In addition, ink compositions containing the dye compound or the mixture are subject to no crystal precipitation, physical changes and color changes in long-term preservation and thus features good storage stability and can present photo-tone color images truthfully in long term; Even images printed on the surface (coated by inorganic particle) of special paper of photo quality (film) are of good fastness of light resistance, ozone resistance and moisture resistance and thus long-term storage stability.

The compounds shown in the general formula (I) or (III) are carbonyl propyl sulfuryl anthrapyridone sulfonic acid compounds in a form of free acid, wherein carbonyl propyl sulfuryl is introduced to the substituted anthrapyridone sulfonic acid compound molecule:

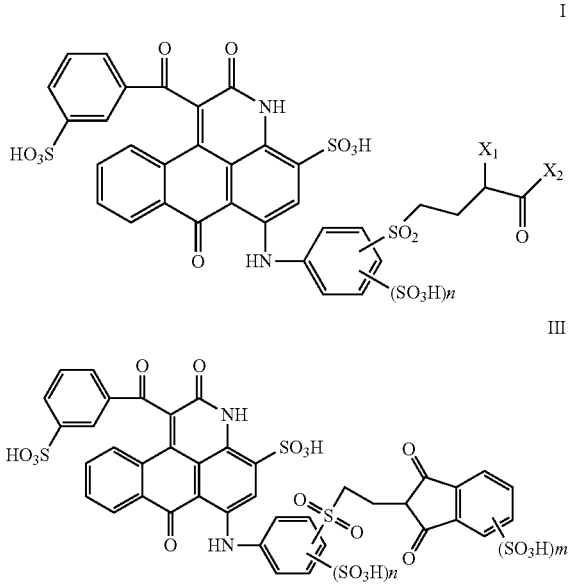

In the general formula (I), the substituent $X_1$ on carbonyl propyl sulfuryl is H or $CO_2H$; $X_2$ is OH or phenyl group with 0-2 sulfonic acid substituents.

When $X_2$ is OH, $X_1$ is H; and when $X_2$ is phenyl group with 0-2 sulfonic acid substituents, $X_1$ is H or $CO_2H$;

Actually, the compounds shown in the general formula (III) are formed as follows: in the compounds shown in the general formula (I), when $X_2$ is phenyl group with 0-2 sulfonic acid substituents and $X_1$ is $CO_2H$, under the heating condition in the sulfonation step in the preparation process, $X_2$ and $X_1$ in a part of compounds form a condensed ring consisting of a five-membered ring and a benzene ring, so as to form the compounds shown in the general formula (III).

In the general formula I and III, sulfonic acid groups $(SO_3H)n$ and $(SO_3H)m$ can be located at any position of the benzene ring, wherein n and m are 0-2, preferably 1-2.

Salts of the compounds of the present invention are selected from the following cation salts preferably: $Li^+$, $Na^+$, $K^+$, $NH_4^+$, or organic ammonium salt $N^+R_1R_2R_3R_4$, of which $R_1, R_2, R_3, R_4$ are respectively the same or different H, $C_{1-18}$ alkyl group, cyclohexyl group, $CH_2CH_2OH$, $CH(CH_3)$ $CH_2OH$ or benzyl group.

(IV') with a sulfonic acid group are used as base raw material. Cyclization reaction is carried out on the base raw material and benzoyl acetic acid ester in an organic solvent to form the intermediate compound shown in the formula (V), then sulfonation and decomposition reactions are carried out to form the mixture of the compounds shown in the general formula (I) and (III), salting-out or salt conversion are carried out to form the salt mixture, and then separation and desalination are carried out to obtain the pure compounds shown in the general formula (I) and (III).

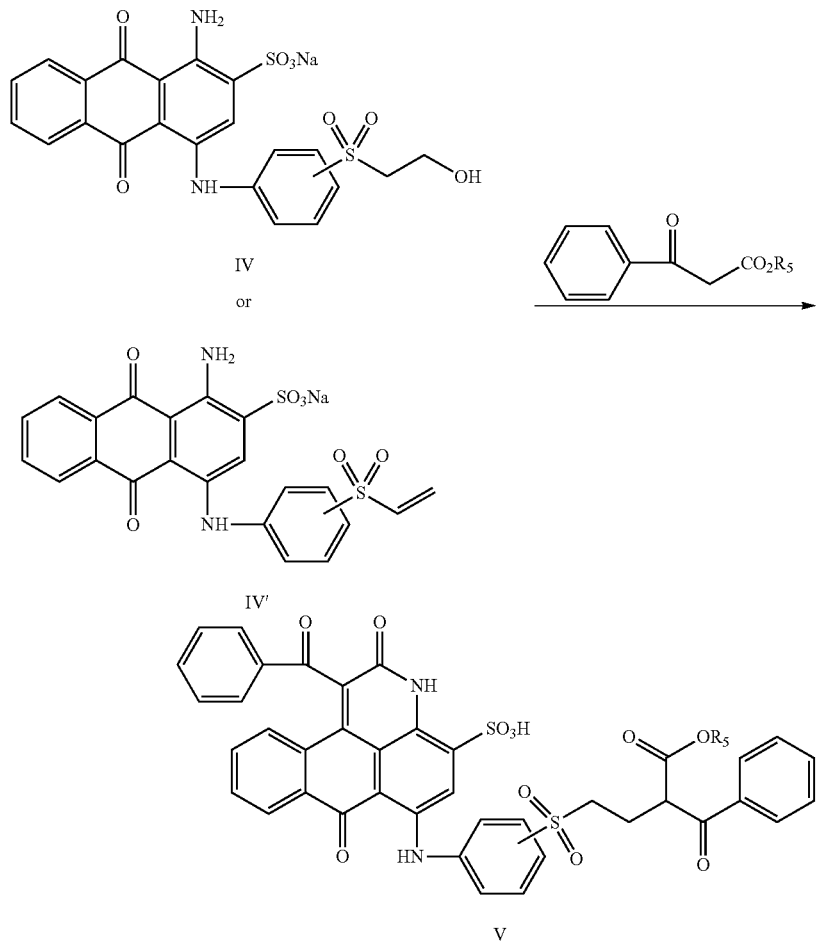

In a preferred embodiment, said organic ammonium salt $N^+R_1R_2R_3R_4$ is selected from: monoethanolamine salt, diethanolamine salt, triethanolamine salt, monoisopropanolamine salt, diisopropanolamine salt or triisopropanolamine salt.

In a more preferred embodiment, said cation is selected from $Li^+$, $Na^+$, $K^+$ or $NH^{4+}$.

The compounds shown in the general formula (I) or (III) or the salts thereof can be used in a mixture form of random ratio in actual application.

Preparation of the Compounds Shown in the General Formula (I) and (III), the Salts Thereof or their Mixtures In preparation of the compound of the present invention, other than the method for preparing other anthrapyridone sulfonic acid compounds by using a non-dye compound as the starting raw material in the prior art, low-cost anthraquinone dye derivatives shown in the formula (IV) or $R_5$ in benzoyl acetic acid ester and the compound shown in the general formula (V) are selected from $C_1$-$C_4$ alkyl group, and preferably methyl group and ethyl group.

The compound shown in the general formula (V) is synthesized by reacting the compound shown in the formula (IV) or (IV') with benzoyl acetic acid ester in an organic solvent with the boiling point of 100-300° C. at the temperature of 100-250° C. for 2-10 h to form the compound shown in the general formula (V).

The benzoyl acetic acid ester is selected from methyl benzoyl acetate, ethyl benzoyl acetate, propyl benzoyl acetate or butyl benzoyl acetate.

The mentioned organic solvent has the boiling point of 100-300° C. and can dissolve or partially dissolve the reaction raw material (IV) or (IV').

In reaction processing, the byproducts water and ethanol $R_5OH$ are discharged from the reaction system under the condition of heating reflux or heating evaporation so as to accelerate the reaction.

Water segregator is used to remove the resulting byproducts water and ethanol from the reflux condenser to promote the reaction.

The end of cyclization reaction can be determined by intra-industry regular methods, e.g., liquid chromatography or thin layer chromatography. Disappearance of characteristic blue peak of the raw material (IV) or (IV') in the liquid chromatogram indicates the end of the reaction.

No special restrictions are placed on the molar ratio of the compound (IV) or (IV') and benzoyl ethyl acetate in cyclization reaction. A proper ratio can be selected by the common technical personnel according to the prior art and common sense. The molar ratio is preferably 1:2-100, preferably 1:2-50, more preferably 1:2-25, still more preferably 1:2-15, still more preferably 1:2-10 and 1:2-5.

Benzoyl acetic acid ester, as one of the raw materials for the reaction, can also be directly used as the reaction solvent. In this case, the consumption of benzoyl acetic acid ester will be greater. The raw material can be selected from ethyl benzoyl acetate, methyl benzoyl acetate, propyl benzoyl acetate or butyl benzoyl acetate to form corresponding compound shown in the general formula (V).

Organic solvents used in the cyclization reaction should be capable of dissolving or partly dissolving the raw material (IV) or (IV') to accelerate the reaction. The byproducts water and alcohol can be discharged from the reaction system by evaporation.

The boiling point of the involved organic solvents is 100-300° C., preferably 140-250° C. and more preferably 140-200° C.

Said organic solvents include but not limited to: toluene, all isomers of dimethylbenzene and its isomer mixture, all isomers of trimethylbenzene and its isomer mixture, all isomers of diethylbenzene and its isomer mixture, all isomers of triethylbenzene and its isomer mixture, petroleum ether, ethylene glycol dimethyl ether, ethylene glycol diethyl ether, ethylene glycol dipropyl ether, ethylene glycol dibutyl ether, 1,2-propylene glycol dimethyl ether, 1,2-propylene glycol diethyl ether, 1,2-propylene glycol dipropyl ether, 1,2-propylene glycol dibutyl ether, diethylene glycol dimethyl ether, diethylene glycol diethyl ether, diethylene glycol dipropyl ether, diethylene glycol dibutyl ether, chlorobenzene, all isomers of dichlorobenzene, mixed dichlorobenzene, dimethyl sulfoxide (DMSO), dimethyl formamide, N-methyl pyrrolidone, sulfolane, and mixture of the above solvents.

Said organic solvents are more preferably selected from: dimethylbenzene, diethylbenzene, trimethylbenzene, chlorobenzene, dichlorobenzene, trichlorobenzene, nitrobenzene, DMSO, DMF, 2-pyrrolidone, NMP, sulfolane and their mixture.

Said organic solvents are most preferably selected from: dimethylbenzene isomer mixture, o-dichlorohenzene, mixed solvent of dimethylbenzene and DMSO and mixed solvent of o-dichlorohenzene and DMSO.

Temperature for the cyclization reaction is 100-250° C., preferably 100-200° C. and more preferably 130-190° C.

The reaction temperature may be increased or regulated under boosting pressure or vacuum conditions, which can adopt atmospheric pressure of 0.5-5 atm.

The cyclization reaction time is preferably 2-8 h, more preferably 2-5 h and still more preferably 2-4 h.

Cool the reaction system to 0-50° C. (preferably 0-30° C.) after the cyclization to separate out the solid-state intermediate compound of general formula (V) from the liquid reaction system to obtain the solid intermediate (V).

During or after the reaction system cools down, add low-boiling point organic solvents to promote full precipitation of the intermediate (V). Preferably low-boiling point organic solvents with boiling point of 30-150° C. have low solubility to the intermediate (V).

Said low boiling point organic solvents include but not limited to: methanol, ethanol, propanol, isopropanol, acetone, methyl ethyl ketone, ethyl ether, tetrahydrofuran, dioxane, dichloromethane, chloroform, carbon tetrachloride, cyclohexane, petroleum ether, ethyl acetate, methyl acetate, butyl acetate, isobutyl acetate, sec-butyl acetate, ethyl formate, propyl formate, butyl formate, isobutyl formate, sec-butyl formate or their mixtures.

The low-boiling point organic solvent is preferably selected from methanol, ethanol, propanol, isopropanol, acetone, acetonitrile, petroleum ether, cyclohexane, or their mixtures, and more preferably methanol, ethanol, propanol, isopropanol, or their mixtures.

Alkalis may be added during cyclization to promote the reaction. Said alkalis may include but not limited to: sodium carbonate, sodium bicarbonate, potassium carbonate, potassium bicarbonate, lithium carbonate, lithium bicarbonate, ammonium carbonate, ammonium bicarbonate, sodium phosphate, disodium hydrogen phosphate, potassium phosphate, dipotassium hydrogen phosphate, ammonium phosphate, diammonium hydrogen phosphate, lithium phosphate, dilithium hydrogen phosphate, sodium acetate, potassium acetate, lithium acetate, ammonium acetate, sodium oxalate, potassium oxalate, lithium oxalate, ammonium oxalate, sodium hydroxide, potassium hydroxide, aluminum hydroxide and lithium hydroxide.

Said alkalis are preferably sodium carbonate or sodium bicarbonate. No special restrictions on addition amount of alkali. However, the molar ratio of compound (IV) and alkalis is preferably 1:0.01-20, more preferably 1:0.05-10, more preferably 1:0.5-5, and still more preferably 1:0.5-2.5.

Sulfonation-Decomposition Reaction of the Intermediate Compound (V)

The sulfonation-decomposition reaction is carried out under the temperature of 10-120° C.

The intermediate compound (V) is sulfonated with fuming sulfuric acid ($SO_3 \cdot H_2SO_4$)) containing 5-30% $SO_3$ or chlorosulfonic acid, and simultaneously decomposition reaction is carried out to obtain a mixture, wherein the mixture comprises the compounds shown in the general formula (I) (when $X_2$ is OH, $X_1$ is H; and when $X_2$ is phenyl group with 0-2 sulfonic acid substituents, $X_1$ is H or $CO_2H$) and the compounds shown in the general formula (III). Decomposition and sulfonation are simultaneously carried out. Multiple decomposition reactions can simultaneously happen during the decomposition process.

The reaction formula of the sulfonation and decomposition process is as follows:

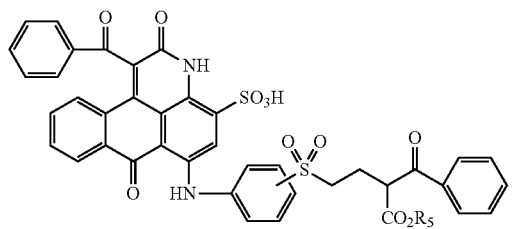

V

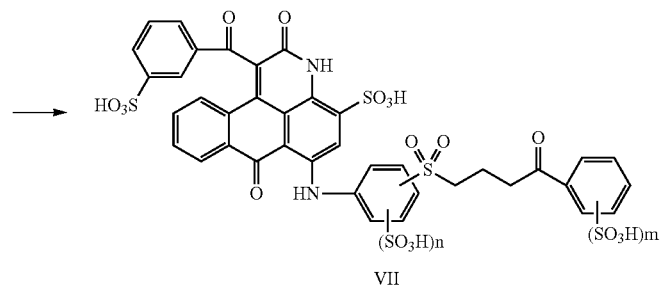

VII

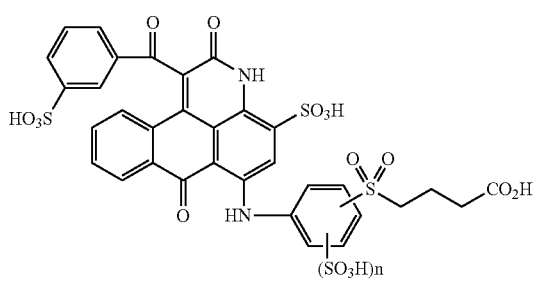

VI

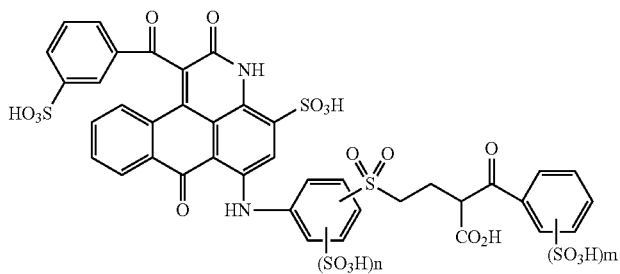

VIII

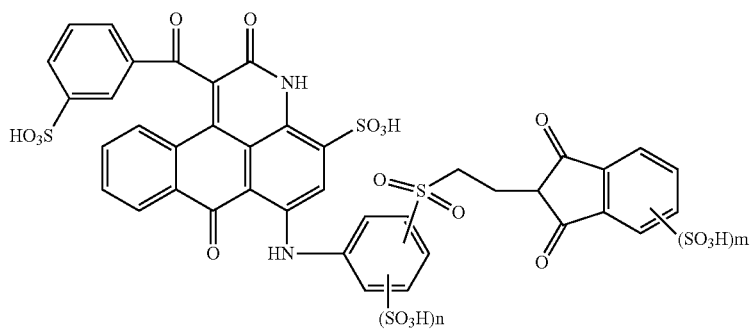

IX

It can be seen from the formula that V is sulfonated and decomposed to generate products VI, VII, VIII and IX, wherein when V is decomposed into VI, the reaction byproducts comprise $R_5OH$, benzoic acid and water; when V is decomposed into VII, the byproducts comprise $HCO_2R$ and water; when V is decomposed into VIII, the byproducts comprise $R_5OH$ and water; when V is decomposed into IX, the byproducts comprise $R_5OH$ and water; and the IX compound is the compound shown in the general formula (III).

Decomposition and sulfonation of the intermediate compound (V) are carried out by using fuming sulfuric acid or chlorosulfonic acid under stirring.

When fuming sulfuric acid is used for sulfonation, the sulfur trioxide content in the fuming sulphuric acid is 5-30%, preferably 5-20%, more preferably 6-15% and the most preferably 7-13%.

No specific restrictions are placed on the dosage ratio of the intermediate (V) to fuming sulfuric acid, the weight ratio of dry intermediate (V) to fuming sulfuric acid is preferably 1:5-50, more preferably 1:20, further more preferably 1:15, and still most preferably 1:10.

The temperature for sulfonation with fuming sulfuric acid is preferably 10-100° C. and more preferably 40-90° C.

When chlorosulfonic acid is used for sulfonation, no specific restrictions are placed on the dosage ratio of the intermediate (V) to chlorosulfonic acid, preferably the molar ratio of the dry intermediate (V) to chlorosulfonic acid preferably 1:3-50 and more preferably 1:5-30.

The temperature for sulfonation with chlorosulfonic acid is preferably 20-100° C., more preferably 10-80° C. and further more preferably 20-60° C.

The reaction time is preferably 2-4 h and more preferably 3-4 h, after which the reaction ends.

The end of the reaction can be determined by intra-industry regular methods, e.g., liquid chromatography or thin layer chromatography. When using liquid chromatography to control end of reaction, determine the end of reaction by using the method of reversed phase ion pair according to the peak retention time of the raw material and the sulfonated product.

The mixture of the compounds shown in the general formula (I) and (III) can be obtained through the above steps. The variety and ratio of the general formula (I) and (III) compounds in the mixture depends on the reaction temperature and time. In the range of the reaction temperature (10-120° C.) and time (2-4 h) of the present invention, the specific compounds shown in the general formula (I) and the compounds shown in the general formula (III) can be formed. In the mixture product, the ratio of each specific compound can change within a range of 0-100%, but cannot be 0% or 100% simultaneously, and the sum of the contents of the compounds in each mixture product is 100% based on the total weight of the mixture product.

The non-limited specific examples of the prepared compounds shown in the general formula (I) are as follows:

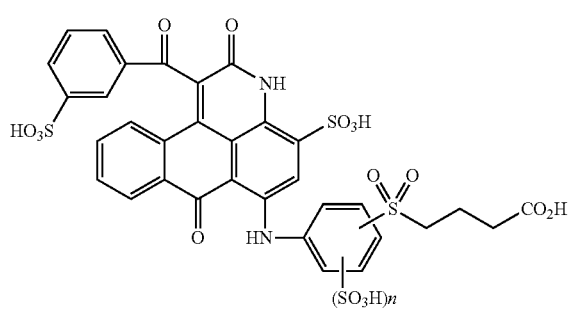

VI

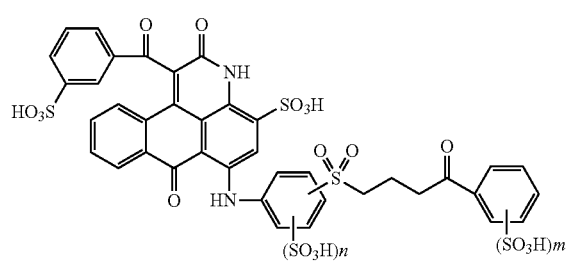

VII

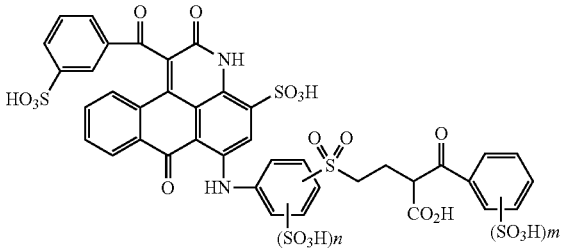

VIII

The mixture obtained by sulfonation and decomposition can be subjected to salting-out or salt conversion so as to form the salt mixture. Salting out and salt conversion can be conducted according to the intra-industry regular practice.

In a preferred embodiment, sulfonated and decomposed products (mixture) are poured into ice water after the sulfonation-decomposition reaction under stirring, controlling the temperature below 40° C. Salting-out or salt conversion is conducted to obtain the salt mixture.

Inorganic salt is preferably adopted to salt-out the obtained compounds shown in the general formula (I) or (III) to form the salts. Said inorganic salts may preferably include but not limited to ammonium chloride, sodium chloride, lithium chloride, etc., or their mixtures.

When the inorganic salt is used for salting-out the sulfonation product (such as the sulfonation product poured into ice water for cooling), multiple salting-out operations are preferably carried out to obtain the mixture of the salts of the compounds shown in the general formula (I) and (III).

Another non-limited specific operation is as follows: For example, after salting out with table salt sodium chloride and filtering, wet cake of sodium salt can be obtained. Dissolve the wet cake in water, add hydrochloric acid to adjust the pH value to 1-2, and filter the solution to obtain crystals, finally obtain the mixture of compounds shown in the general formula I and III in the form of free acids (or partially sodium salt). Then Stir the wet cake of the free acids with water, add alkalis such as potassium hydroxide, lithium hydroxide, ammonia, or organic amines and so on for neutralization, and add salts for salting out to obtain potassium salt, lithium salt, ammonium salt or organic ammonium salt correspondingly. Among these salts, lithium salt, sodium salt and ammonium salt are preferred.

Another non-limited specific operation is as follows: adding water and lime (calcium hydroxide) to the sulfonation product poured into ice water to neutralize sulfuric acid in the reaction system at the temperature below 40° C. until pH is neutral so as to form calcium sulfate precipitate, filtering and washing the filter cake with water to be colorless, combining filtrate and washing liquid, adding NaOH until the pH reaches 12-14, stirring for 2 h, then adjusting the pH to be neutral with citric acid, filtering out generated precipitate to obtain the mixture of sodium salts of the compounds shown in the general formula (I) and (III), and then concentrating and separating.

The obtained mixture of the salts of the compounds shown in the general formula (I) and (III) can be separated by adopting conventional separation means, such as adsorption chromatography separation method, stepped salting-out separation method, reversed phase ion pair chromatography and so on.

Taking the reversed phase ion pair chromatography as an example, the reversed phase ion pair uses tetrabutyl ammonium bromide, tetrabutyl ammonium iodide, triethylamine acetate and the like, and the sulfonic acid group on the dye molecule to form hydrophobic ion pair. As the polarity of the dye, the number of the sulfonic acid groups and the molecular weight of the dye are different; the ion pair has different adsorptive capacities to an adsorbent (such as octadecyl silanized filler). Therefore, the compounds in the mixture can be separated by adopting methanol-water as eluent through gradient elution technology according to the different eluting sequences of the reversed phase ion pair in a chromatographic column. Specific operations: eluting the product of strong polarity, multiple sulfonic acid groups and small molecular weight with a strong-polarity solvent containing more water and less methanol (such as 5% methanol), gradually increasing the methanol ratio (from 5% to 100%), and finally eluting the product of small polarity, few sulfonic acid groups and large molecular weight. According to different eluting sequences, the separated and purified products, namely the salts of the compounds shown in the general formula (I) and (III), can be obtained by collecting the eluates at different time intervals.

The salts of the compounds obtained by separation can be respectively desalinated to obtain the compounds shown in the general formula (I) and (III).

Desalination can be conducted by adopting intra-industry conventional method, such as high-pressure reverse osmosis membrane method.

Actually, in actual application, the mixture product can be directly applied without separation. The application effect of the mixture is even superior to the pure compounds at times because the mixture has high solubility, high color density and full color after printing. The said mixture can be mixture of the salts of the compounds shown in the general formula (I) and (III), or mixture of the compounds shown in the general formula (I) and (III).

In the synthesis method of the present invention, the blue commercial dye compound of the general formula (IV) and (IV') as the raw material can be prepared from a commercial reactive dye through heating in water or organic solvent under the alkaling condition. For example, commercially purchased reactive blue 19 (RB19) with sulfuryl at the meta-position of amino can be converted into IV-RB19 or IV'-RB19, corresponding to IV or IV', under the alkaling condition in a conventional method. IV-RB19 or IV'-RB19 further reacts with benzoyl acetic acid ester to form V-RB19, corresponding to the intermediate V ($R_5$ is ethyl). In a similar way, the blue dye with sulfuryl at the p-position of amino can also be used as a starting raw material.

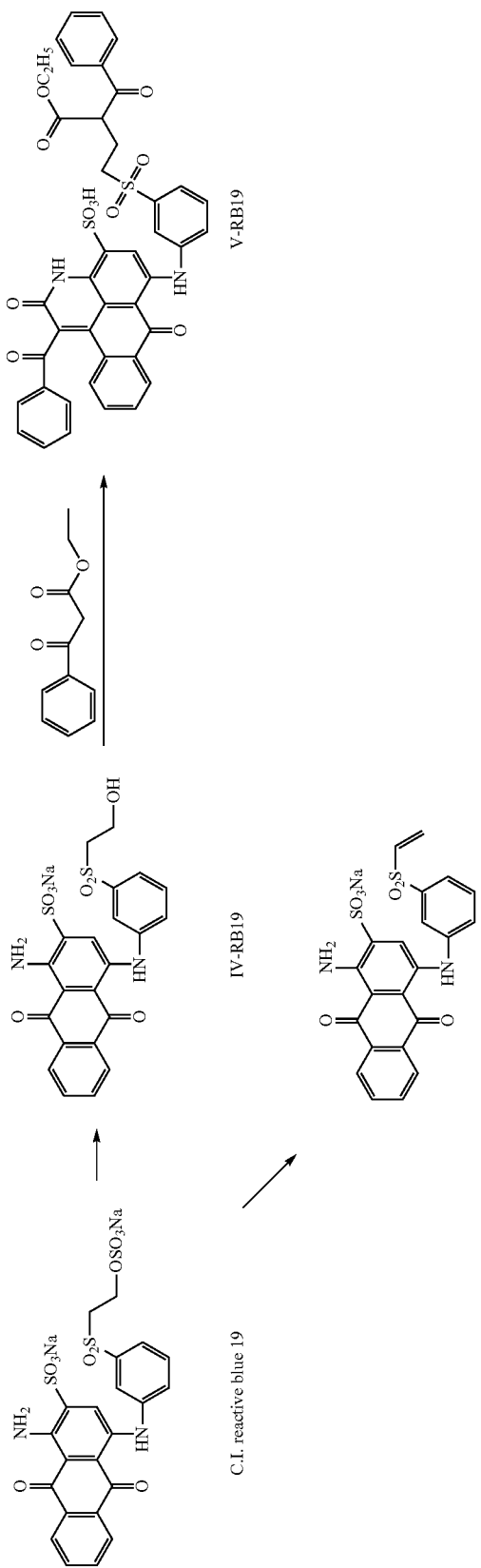

Specific examples (in a form of free sulfonic acid) of compounds of general formula (I) and (III) prepared in the above method include the followings (the present invention is not limited to compounds of these structures):
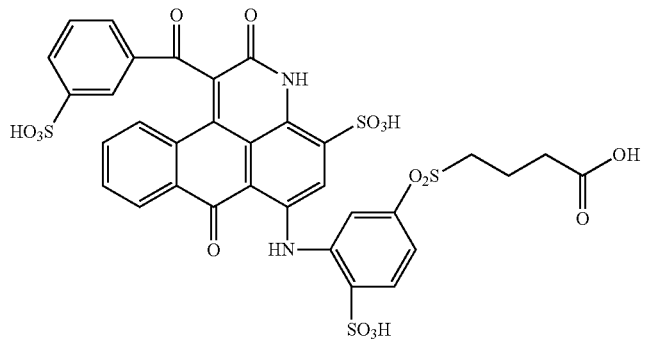
Dm1
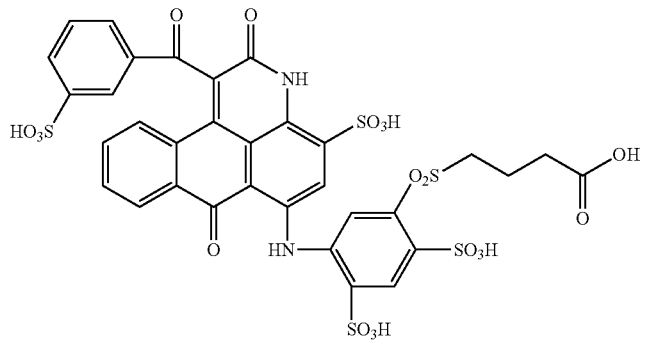
Dm2
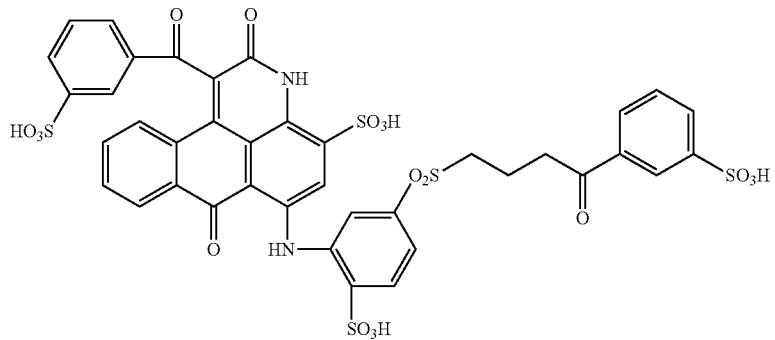
Dm3
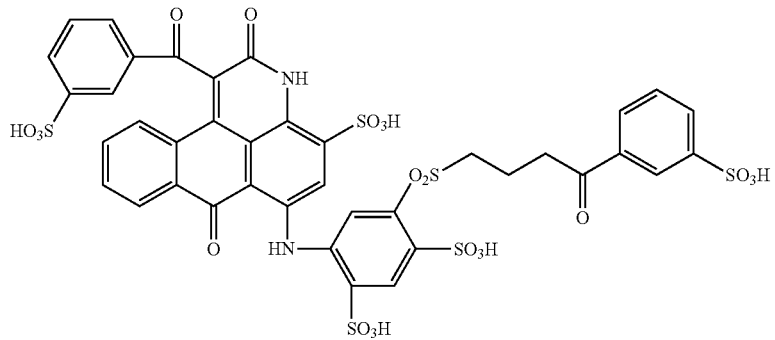
Dm4

-continued
Dm5
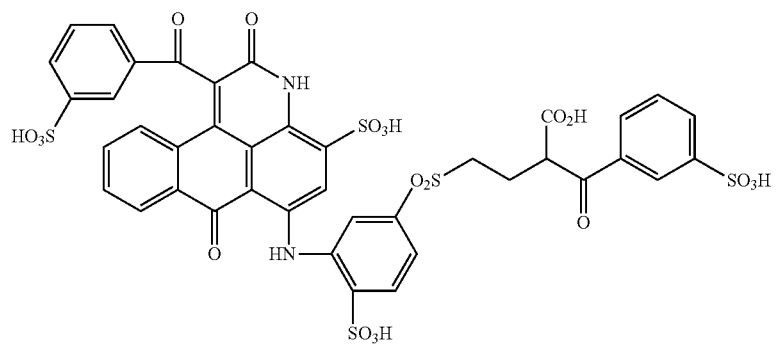
Dm6
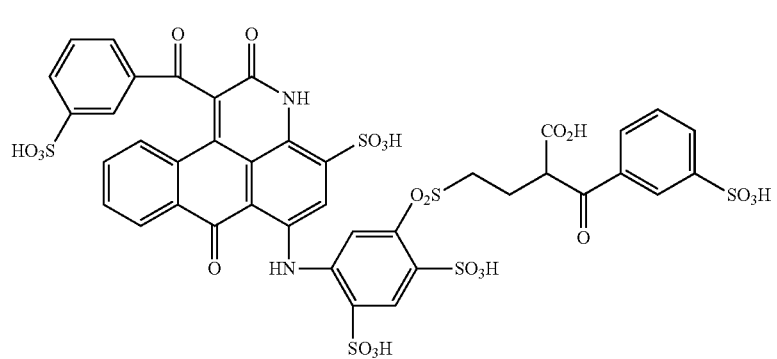
Dm7
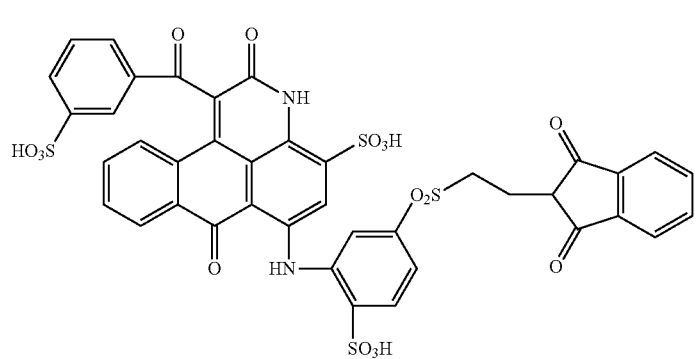
Dm8
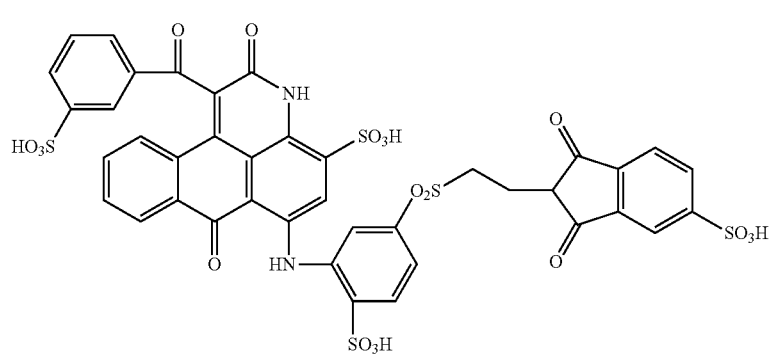

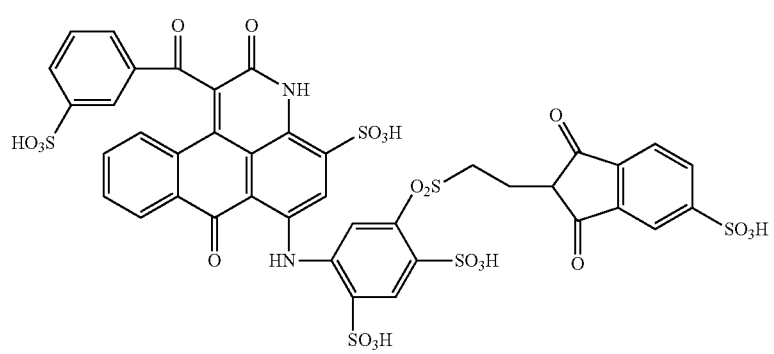
Dm9
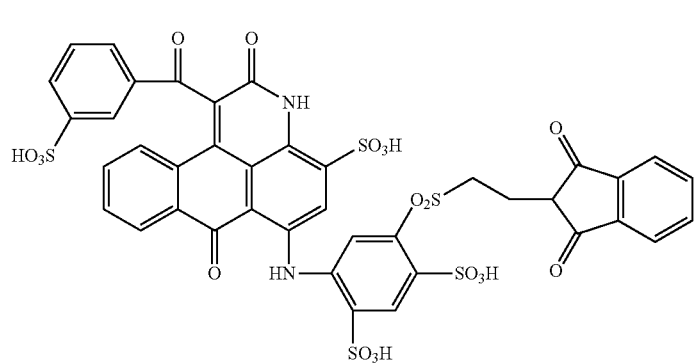
Dm10
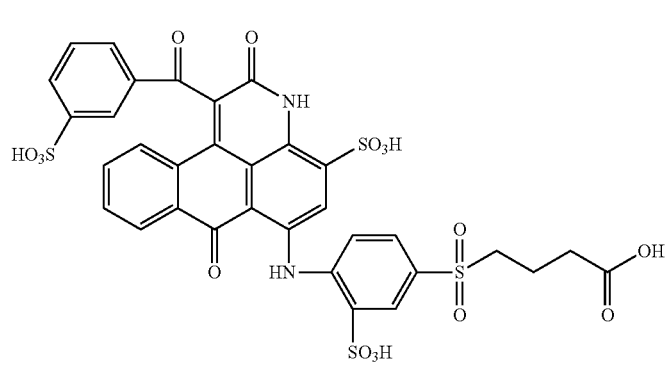
Dp1
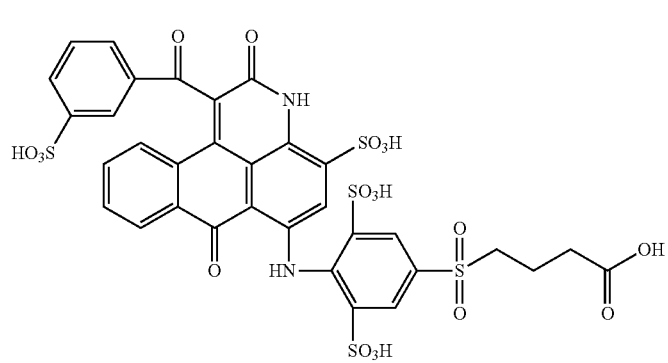
Dp2

-continued
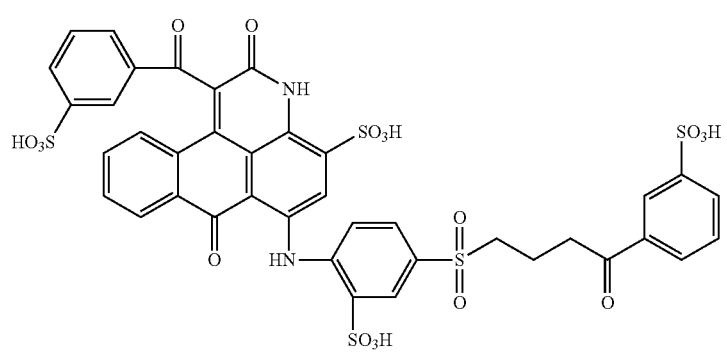
Dp3
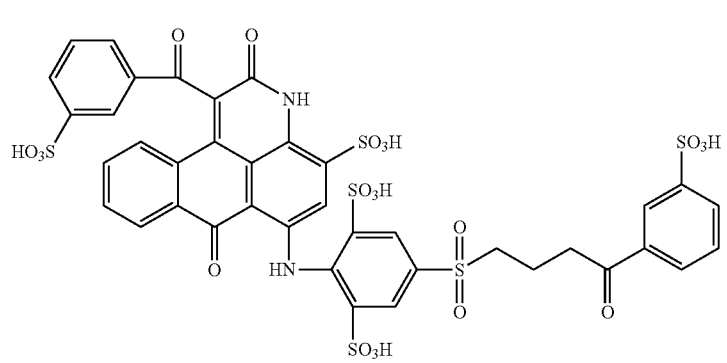
Dp4
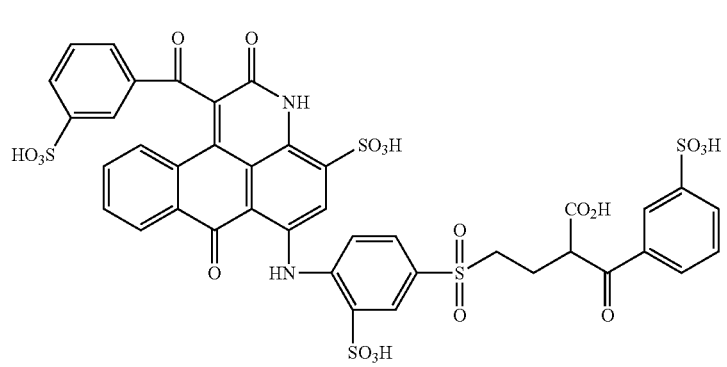
Dp5
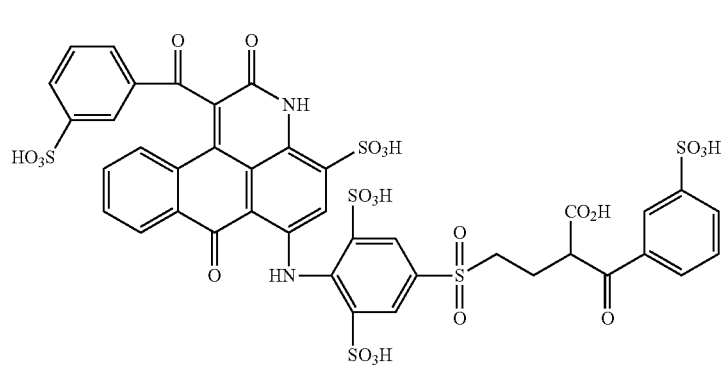
Dp6

-continued
Dp7
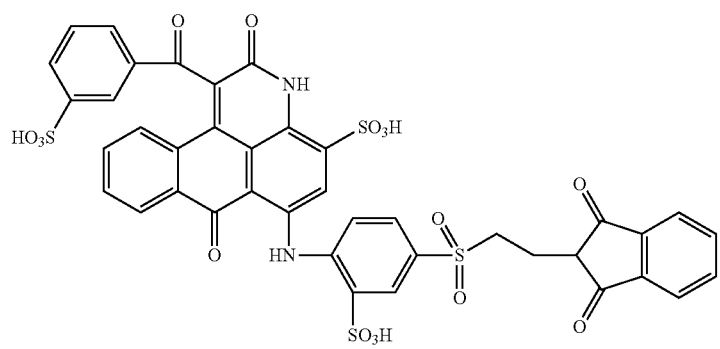
Dp8
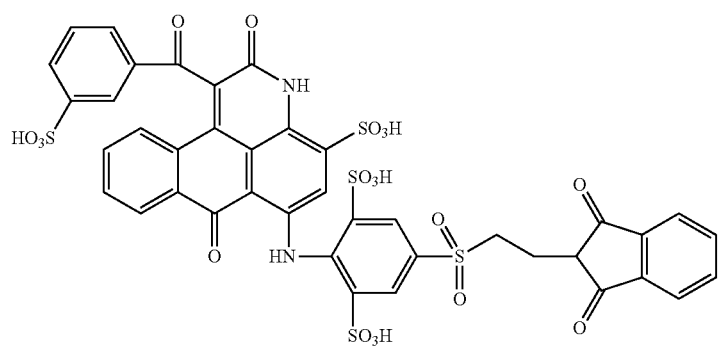
Dp9
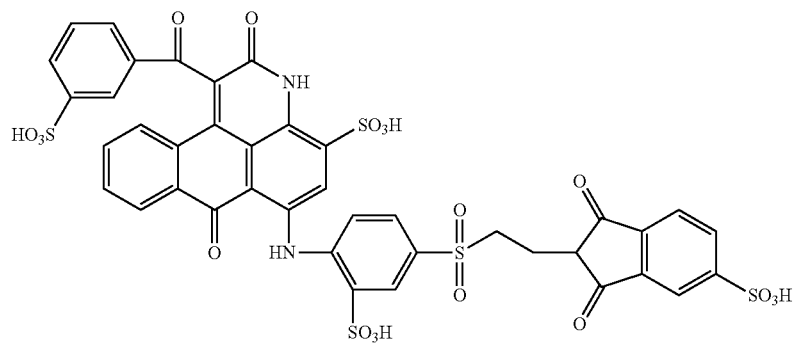
Dp10
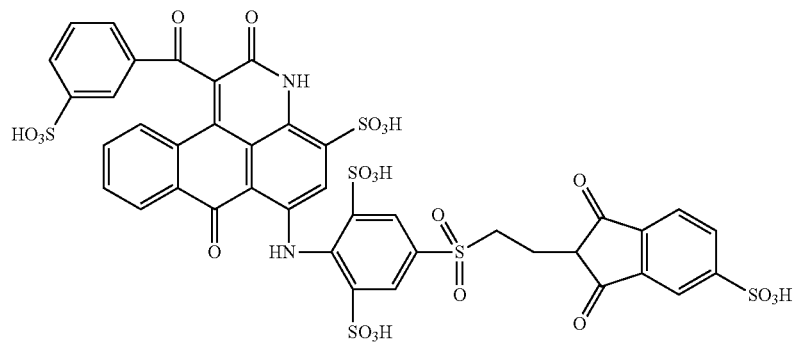
The products prepared in the above method, namely the compounds shown in the general formula (I) and (III), the salts thereof or their mixture, contain the inorganic salt content being preferably below 1 wt %. Conventional method like high pressure reverse osmosis membrane can be used for desalination of the dyes to obtain the aforesaid salt content.

The compounds shown in the general formula (I) or (III), the salts thereof or their mixtures can be used as dyes and dissolved in water or aqueous solvent (water containing the following water-soluble organic solvent) so as to prepare the ink composition. Dosage of dyes compounds or their mixtures of the present invention is generally 0.1-20 wt %, preferably 1-20 wt %, more preferably 1-15 wt %, and further more preferably 2-10 wt %.

Based on the total weight of the components in the ink composition, the aforesaid ink composition also contains 0-50% of water soluble or water-miscible organic solvents by weight, preferably 5-50%, and 0-5 wt % of ink control agents. The rest component is water.

Specific examples of water soluble or water-miscible organic solvents of the present invention include: $C_1$ to $C_4$ alkanol such as methanol, ethanol, n-propanol, isopropanol, butanol, isobutanol, sec-butanol, tert-butanol, etc.; carboxylic acid amides such as N,N-dimethyl formamide or N,N-dimethyl acetamide, etc.; lactams such as 2-pyrrolidone, N-methyl-2-pyrrolidone, etc.; nitrogen-containing cyclic solvents such as 1,3-dimethyl imidazoline-2-ketone or 1,3-dimethyl hexahydro pyrimidine-2-ketone, etc; ketones such as acetone, methyl ethyl ketone, 2-methyl-2-hydroxy penta-4-ketone, etc.; cyclic ethers such as tetrahydrofuran, dioxane, etc.; ethylene glycol, 1,2- or 1,3-propanediol, 1,2- or 1,4-butanediol, 1,6-hexanediol. Monomers and oligomers with (C2 to C6) alkylidene units, e.g., diethylene glycol, triethylene glycol, tetraethylene glycol, dipropylene glycol, sulfur glycol, polyethylene glycol, polypropylene glycol or polyalkylene glycol or thioglycol, etc.; polyols (triols) such as glycerol, hexane-1,2,6-triol, etc.; C1 to C4 alkyl ethers of polyols such as ethylene glycol monomethyl ether or ethylene glycol monoethyl ether, diethylene glycol monomethyl ether, diethylene glycol monobutyl ether, diethylene glycol monoethyl ether, triethylene glycol monomethyl ether, triethylene glycol monoethyl ether, etc.; γ-butyrolactone or dimethyl sulfoxide, etc. These organic solvents can be used alone or in combination.

The organic solvent is preferably 2-pyrrolidone, N-methyl-2-pyrrolidone, ethylene glycol, diethylene glycol, triethylene glycol or dipropylene glycol, and more preferably 2-pyrrolidone, N-methyl-2-pyrrolidone or diethylene glycol.

The ink composition can also contain the ink control agent.

Specific examples of ink control agents: antiseptic antimildew agents, pH adjusting agents, chelating reagent, rust inhibitors, water-soluble ultraviolet absorbent, water soluble polymers, dye dissolving agent, surfactant.

Examples of antiseptic antimildew agents: organic sulfurs, organic nitrogen sulfurs, organic halogens, allyl sulfone halides, iodo allylene, N-haloalkyl-based sulfurs, nitriles, pyridines, 8-hydroxyquinoline, benzothiazoles, isothiazolizones, dithiols, pyridine oxides, nitropropanes, organotins, phenols, quaternary ammonium salts, triazines, diazthines, anilides, adamantanes, dithiocarbamates, hydrindone bromizes, benzyl bromacetates, inorganic salts, etc. Examples of organic halogen compounds: sodium pentachlorophenol; examples of pyridine oxide compounds: 2-pyridine thiol-1-sodium oxide; examples of inorganic salt compounds: anhydrous sodium acetate; examples of isothiazolines: 1,2-benzisothiazoline-3-ketone, 2-octyl-4-isothiazoline-3-ketone, 5-chloro-2-methyl-4-isothiazoline-3-ketone, 5-chloro-2-methyl-4-isothiazoline-3-ketone magnesium chloride, 5-chloro-2-methyl-4-isothiazoline-3-ketone calcium chloride, 2-methyl-4-isothiazoline-3-ketone calcium chloride Other antiseptic antimildew agents include: sodium sorbate, sodium benzoate, etc.

pH adjusting agent is any substance to control pH of the ink between 7.0 and 11.0. Examples include: alkanolamines such as diethanolamine, triethanolamine, etc.; alkali metal hydroxides such as lithium hydroxide, sodium hydroxide, potassium hydroxide, etc.; ammonium hydroxide or ammonia; or alkali metal carbonates such as lithium carbonate, sodium carbonate, potassium carbonate, etc. Among these pH adjusting agents, ammonia is preferred.

Examples of chelating reagents include: sodium ethylene diamine tetracetate, nitro sodium triacetate, sodium hydroxyethyl ethylenediamine triacetate, diethylenetriaminepentaacetic acid pentasodium salt, dialuramide sodium diacetate, etc.

Examples of rust inhibitors include: bisulfite, sodium thiosulfate, ammonium thioglycolate, nitrosodiisopropylamine, pentaerythritol tetranitrate, dicyclohexylamine nitrite, etc.

Examples of water-soluble ultraviolet absorbent include: sulfonated benzophenone or sulfonated benzotriazole, etc.

Examples of water soluble polymers include: polyvinyl alcohol, cellulose derivatives, polyamines, polyimine, etc.

Examples of dye dissolving agent include: urea, ε-caprolactam, diethyl carbonate, etc.

Examples of surfactants include: anionic surfactants, amphoteric surfactants, cationic surfactants, non-ionic surfactants, etc. Examples of the anionic surfactant be cited such as: alkyl sulfo carboxylate, α-olefin sulfonates, polyoxyethylene alkyl ether acetates, N-acyl amino acid and its salts. N-acyl methyl taurine, citronellic soap, castor oil sulfate, ammonium lauryl sulfate, alkylphenol type phosphate, alkyl type phosphate, alkylallyl sulfonate, diethyl sulfosuccinate, diethylhexyl sulfosuccinate, dioctyl sulfosuccinate, etc. Examples of cationic surfactants may include: 2-vinylpyridine derivatives, poly-4-vinylpyridine derivatives, etc. Examples of amphoteric surfactant include: lauryl dimethyl amino acetic acid lycine, 2-alkyl-N-carboxymethyl-N-hydroxyethyl imidazoline onium betaine, coco fatty amidepropyldimethylamieno acetic acid betaine, other imidazoline derivatives polyoctyl polyaminoethyl glycine, etc. Examples of non-ionic surfactants include: ethers such as polyoxyethylene nonylphenyl ether, polyoxyethylene octylphenyl ether, polyoxyethylene laurylphenyl ether, polyoxyethylene octylphenyl ether, polyoxyethylene oil-based ether, polyoxyethylene lauryl ether, polyoxyethylene alkyl ether, etc; esters such as polyoxyethylene oleic acid, polyoxyethylene oleic acid ester, polyoxyethylene distearate, sorbitan laurate, sorbitan monostearate, sorbitan monooleate, sorbitan sesquioleate, polyoxyethylene monooleate, polyoxyethylene stearate, etc; 2,4,7,9-tetramethyl-5-decyne 4,7-diol, 3,6-dimethyl-4-octyne-3,6-diol, alkyl acetylenic diols such as 3,5-dimethyl-1-hexyne-diol (e.g., Surfynol 104, 82, 465, Olfine STG, etc., manufactured by Rixin Chemicals), etc. These ink control agents can be used alone or in combination.

The ink composition of the present invention is prepared by dissolving the dye compounds shown in the general formula (I) or (III), the salts or their mixtures into water or the above described aqueous solvents (water containing water-soluble organic solvents) or water-miscible organic solvents with the above described ink control agents as necessary.

No specific restrictions are placed on the order of dissolution of the components in the above preparation methods. The dyes can be preliminarily dissolved in water or the above described aqueous solvents (water containing organic solvents) with addition of ink control agents, or the dyes can be firstly dissolved in water followed by addition of aqueous solvents and ink control agents. Other orders are allowed. The ink composition can also be manufactured by adding aqueous solvents and ink control agents to the solution prepared from reaction liquid containing the dyes or solution containing the pigments via reverse osmosis membrane treatment. Water used for preparation of the ink composition is preferably ion exchange water or deionized water with fewer impurities such as distilled water. Membrane filter can be used for microfiltration to remove inclusions. The filter membrane pore size is generally 1 micron to 0.01 micron, preferably 0.8 microns to 0.2 microns.

The magenta ink composition prepared by carbonyl propyl sulfuryl anthrapyridone sulfonic acid compounds, the salts thereof or their mixtures is suitable for sealing, photocopying, marking, note-taking, drawing, stamping or printing, especially for ink-jet printing. The advantages include that the resulting images have excellent resistance to water, sunlight, ozone and friction, can also be used for toning, in particular, for composition of black dyes.

The dye compounds shown in the general formulas (I) or (III), the salts thereof or their mixtures can be used as coloring agents for paper, fiber or cloth (cellulose, nylon, wool, etc.), leather, color filter substrate, etc. Examples of coloring methods include: printing methods such as dip dyeing, printing and dyeing, screen printing, etc., and ink-jet printing method, among which ink-jet printing method is preferred. The recorded media suitable for the ink-jet printing method can be paper, thin film and other information transmission sheets, fiber, leather, etc. Information transmission sheets are generally subject to surface treatment and an ink-absorbing layer is set in their substrate. The ink-absorbing layer can be formed by dipping or coating cations and other polymers on the above mentioned substrate, and the coating contains porous silica, alumina sol or special ceramics, etc.; these white inorganics are coated on the above described substrates together with polyvinyl alcohol, polyvinylpyrrolidone or other hydrophilic polymers. Thin sheets coated with such ink absorbing layer are generally referred to as special inkjet paper (film) or glossy paper (film), e.g., professional glossy paper, top-class glossy paper, polishing paper (Canon), photo glossy paper, glossy packing paper, superfine special glossy film (Epson), high-quality lustering paper, high-quality glossy film, light paper (HP), etc. In addition, the ink-jet printing method of the present invention is naturally applicable for ordinary paper.

Generally, images printed on substrates coated with porous white inorganics are subject to significant discoloration caused by ozone. Due to the outstanding resistance to gases, the water-based magenta ink composition of the present invention has a special effect on printing on such substrates.

Examples of porous white inorganics include: alcium carbonate, kaolin, talcum, clay, diatomite, synthetic amorphous silicon dioxide, aluminum silicate, magnesium silicate, calcium silicate, aluminum hydroxide, alumina, lithopone stone, zeolite, barium sulfate, calcium sulfate, titanium dioxide, zinc sulfide, zinc carbonate, etc.

In ink-jet printing, in addition to common-used yellow and cyan ink composition, green ink composition, orange ink composition, blue (or purple) ink composition, and magenta ink composition are available. The dye compound of the present invention can be used to prepare magenta ink composition. These color compositions can be used in combination where necessary to prepare black ink composition. The different color ink compositions are filled into corresponding ink cartridges, which are installed at the established position of the inkjet printer for printing. Examples of ink-jet printers include: piezoelectric printer, thermal bubble jet printer, etc.

The magenta ink composition of the present invention is bright magenta in color and shows highly bright tone on glossy inkjet paper as well as high fastness of printed images and security to human health.

No precipitation or separation will occur to the ink composition of the present invention during storage. The ink will not block the nozzles in ink-jet printing, either. Even used by continuous ink-jet printers for a relatively long fix time or intermittently, the ink of the present invention is subject to no changes of physical properties.

Embodiments are provided below to detail the present invention. Unless otherwise specified, "parts" and "%" involved in this application are based on weight.

Embodiments

Embodiment 1

(1) Add 100 parts of dimethyl sulfoxide to 350 parts of o-dichlorohenzene, and while stirring, add 160 parts of derivatives (sodium salt, shown in formula V'-RB19) of (C.I. Reactive Blue 19), 10 parts of sodium carbonate and 250 parts of benzoyl ethyl acetate and heat the mixture up. React the mixture at 175 to 180° C. for 4 h, where water and ethanol produced as byproduct during the reaction are discharged from the reaction system by azeotropic distillation; the color will gradually turns from blue to reddish purple and the end of the reaction will be detected with a liquid chromatograph (about 4 h). Cool down the mixture to below 60° C. and add 800 parts of isopropanol and stir it for 30 min; filter and separate out the precipitates, wash with 500 parts of isopropanol and dry the precipitates to obtain 225 parts of pink purple crystalline V-RB19 (sodium salt). Its maximum absorption in water is 548 nm; mass spectrum: m/z(−): 803.2 ([M-H]$^{-1}$). The most abundant precise molecular mass (M) of the intermediate dye product V-RB19 (calculated by free sulfonic acid) is 804.1

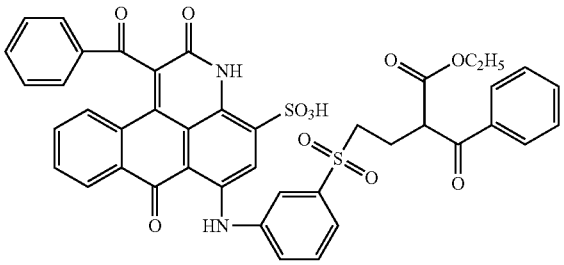

V-RB19

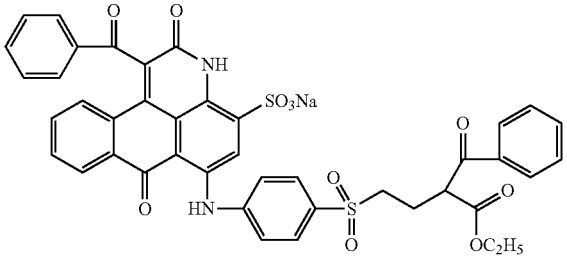

V'-RB-19

(2) After the mixture cools down, add 380.0 parts of 50% fuming sulphuric acid to 450.0 parts of 95.0% sulfuric acid while stirring to obtain 830 parts of 10% fuming sulphuric acid. After the mixture cools down, add 175 parts of sodium salt of the above described compound V-RB19 at the temperature not higher than 40° C. and heat it up. Conduct sulfonation reaction at 60-65° C. for 4 h. After the reaction liquid cools down, slowly pour it to 1,400 parts of ice water while stirring and controlling the temperature below 40° C.; add 750 parts of calcium hydroxide and maintain the temperature below 40° C. with ice blocks, filter the generated calcium sulfate and wash with a small amount of water. Adjust the pH value of the filtrate to 9-10 with 20% sodium hydroxide in ice water bath and obtain about 2,600 parts of solution containing 185 parts of dyes (M1, in a form of sodium salt). The maximum absorption wavelength of the mixed dye M1 in water is 537 nm.

Reversed phase ion pair liquid chromatography is adopted, aφ80 mm C18 chromatographic column (with height of 3000 mm) is used, and methanol of different ratios (linear ratio) is added to a 2 mM acetic acid-triethylamine aqueous solution system to be used as a solvent for eluting (methanol is increased from 15% to 85%). Under the pressure of 20-50 atm, eluting is carried out for 5 h at a flow rate of 100 L/h. Different products are eluted out at different time, a Dm4 pure compound with five charges (five sulfonic acid groups) is firstly eluted and separated out (the collecting time interval is 30th-70th min), then dyes with four charges, namely a Dm3 pure compound (the collecting time interval is 80th-120th min) and a Dm8 pure compound (the collecting time interval is 150th-200th min) are sequentially eluted and separated out, then a Dm1 pure compound with three charges (the collecting time interval is 220th-280th min) is eluted and separated out, and finally the partial low sulfonation degree impurity Dm11 or Dm12 is eluted. The pure product solutions can be obtained by collecting the eluates at different time. Then the obtained solutions are respectively concentrated into 15% solution, hydrochloric acid is added to adjust the pH to 1-2, 10% NaOH is added by volume, concentrating to 30%, then cooling, and the dyes are eluted, filtered and dried to obtain the products containing little NaCl.

During high-performance liquid chromatography (HPLC) analysis, using commercial Betasil C18 (2.1×150 mm) chromatographic column, 2 mM acetic acid-triethylamine aqueous solution system (cation system) is used for linear eluting within 50 min at a flow rate of 0.2 mL/min (methanol is increased from 15% to 85%), and under 550 nm detection wavelength, the content and ratio of the dye compounds (in the form of sodium salt) in the obtained mixture are as follows: Dm1 (13.0%), Dm3 (44.0%), Dm4 (4.5%), Dm8 (18.0%) and Dm10 (18.0%).

Dm1: yield is 22.1 g; the maximum absorption wavelength in aqueous solution is 537 nm, and mass spectrum (EI-MS) m/z(−) is as follows: 415.0 ([$\overline{M}$-2H]$^{2-}$/2), 831.0 ([$\overline{M}$-H]$^{-1}$); The most abundant precise molecular mass ($\overline{M}$) of dye Dm1 (calculated by free sulfonic acid) is 832.0.

Dm3: yield is 77.2 g; the maximum absorption wavelength in aqueous solution is 537 nm, and mass spectrum (EI-MS) m/z(−) is as follows: 323.0 ([$\overline{M}$-3H]$^{3-}$/3), 485.0 ([$\overline{M}$-2H]$^{2-}$/2), 971.0 ([$\overline{M}$-H]$^{-1}$). The most abundant precise molecular mass ($\overline{M}$) of dye Dm3 (calculated by free sulfonic acid) is 972.0.

Dm4: yield is 6.2 g; the maximum absorption wavelength in aqueous solution is 533 nm, and mass spectrum (EI-MS) m/z(−) is as follows: 350.1 ([$\overline{M}$-3H]$^{3-}$/3), 525.0 ([$\overline{M}$-2H]$^{2-}$/2), 1050.9 ([$\overline{M}$-H]$^{-1}$). The most abundant precise molecular mass ($\overline{M}$) of dye Dm4 (calculated by free sulfonic acid) is 1052.0.

Dm8: yield is 30.5 g; the maximum absorption wavelength in aqueous solution is 537 nm, and mass spectrum (EI-MS) m/z(−) is as follows: 332.0 ([$\overline{M}$-3H]$^{3-}$/3), 498.0 ([$\overline{M}$-2H]$^{2-}$/2), 997.0 ([$\overline{M}$-H]$^{-1}$). The most abundant precise molecular mass ($\overline{M}$) of dye Dm8 (calculated by free sulfonic acid) is 998.0.

Dm10: yield is 29.4 g; the maximum absorption wavelength in aqueous solution is 537 nm, and mass spectrum (EI-MS) m/z(−) is as follows: 497.6 ([$\overline{M}$-2H]$^{2-}$/2), 996.9 ([$\overline{M}$-H]$^{-1}$); The most abundant precise molecular mass ($\overline{M}$) of dye Dm10 (calculated by free sulfonic acid) is 998.0.

The other little dye is mixture of Dm11 and Dm12 and is finally eluted out. Dm11 and Dm12 are mutual isomers; the maximum absorption wavelength in aqueous solution is 537 nm, and mass spectrum (EI-MS) m/z(−) is as follows: 445.0 ([$\overline{M}$-2H]$^{2-}$/2) and 891.0 ([$\overline{M}$-H]$^{-1}$); and the most abundant accurate molecular mass $\overline{M}$ is 892.0.

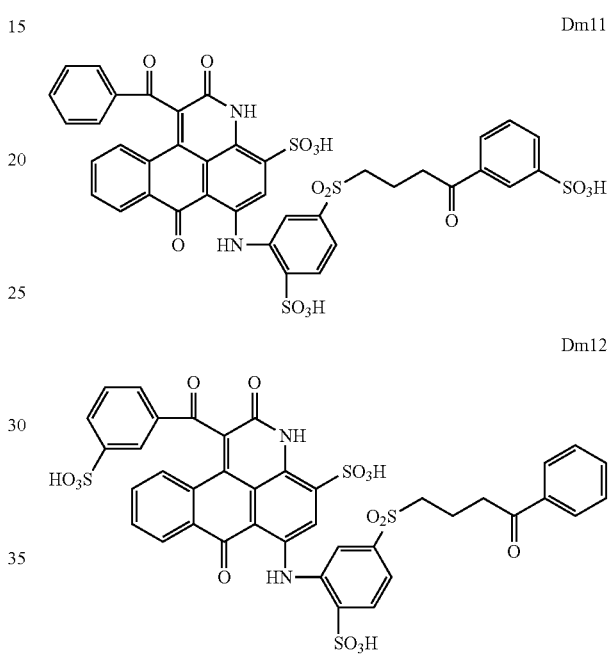

Embodiment 2

The sodium salt of the intermediate V-RB19 is prepared according to the same method as the step 1 in the embodiment 1. Then in the sulfonation reaction of step 2, 10% SO$_3$.H$_2$SO$_4$ is replaced with 12% SO$_3$.H$_2$SO$_4$, the reaction temperature is raised to 85-90° C., and desalination is carried out according to the same method as the step 2 in the embodiment 1 to obtain 2600 parts of solution containing 185 parts of mixed dye (M2 in the form of sodium salt), wherein the maximum absorption wavelength in water is 533 nm.

The dye compounds in the dye mixture M2 are separated by adopting reversed phase ion pair liquid chromatography according to the same separation device and manner as the embodiment 1. A Dm6 pure compound with six charges is firstly eluted and separated out, then dyes with five charges, namely a Dm2 pure compound and a Dm4 pure compound are sequentially eluted and separated out, and then dyes with four charges, namely a Dm8 pure compound and a Dm10 pure compound are sequentially eluted and separated out.

During high-performance liquid chromatography (HPLC) analysis, the same device and manner as the embodiment 1 are adopted, and the content and ratio of the dye compounds (in the form of sodium salt) in the obtained dye mixture M2 are as follows: Dm2 (16.0%), Dm4 (12.5%), Dm6 (6.0%), Dm8 (13.0%), Dm10 (36.0%).

Dm2: yield is 25.0 g; the maximum absorption wavelength in aqueous solution is 537 nm, and mass spectrum (EI-MS) m/z(−): 303.2 ([M-3H]$^{3-}$/3), 455.0 ([M-2H]$^{2-}$/2), 911.0 ([M-H]$^{-1}$). The most abundant precise molecular mass (M) of dye Dm2 (calculated by free sulfonic acid) is 912.0.

Dm4: yield is 20.1 g; the maximum absorption wavelength in aqueous solution is 533 nm, and mass spectrum (EI-MS) m/z(−) is as follows: 350.1 ([M-3H]$^{3-}$/3), 525.0 ([M-2H]$^{2-}$/2), 1050.9 ([M-H]$^{-1}$). The most abundant precise molecular mass (M) of dye Dm4 (calculated by free sulfonic acid) is 1052.0.

Dm6: yield is 10.1 g; the maximum absorption wavelength in aqueous solution is 528 nm, and mass spectrum (EI-MS) m/z(−): 364.4 ([M-3H]$^{3-}$/3), 547.0 ([M-2H]$^{2-}$/2), 1094.9 ([M-H]$^{-1}$). The most abundant precise molecular mass (M) of dye Dm6 (calculated by free sulfonic acid) is 1095.9.

Dm8: yield is 22.2 g; the maximum absorption wavelength in aqueous solution is 537 nm, and mass spectrum (EI-MS) m/z(−) is as follows: 332.0 ([M-3H]$^{3-}$/3), 498.0 ([M-2H]$^{2-}$/2), 997.0 ([M-H]$^{-1}$). The most abundant precise molecular mass (M) of dye Dm8 (calculated by free sulfonic acid) is 998.0.

Dm10: yield is 60.5 g; the maximum absorption wavelength in aqueous solution is 537 nm, and mass spectrum (EI-MS) m/z(−) is as follows: 497.6 ([M-2H]$^{2-}$/2), 996.9 ([M-H]$^{-1}$); The most abundant precise molecular mass (M) of dye Dm10 (calculated by free sulfonic acid) is 998.0.

The other little dye is firstly eluted out and excessively sulfonated which comprises:

Based on free sulfonic acid form, Dm13, Dm14 or Dm15 with molecular weight of 992 are mutual isomers; the maximum absorption wavelength of Dm13, Dm14 or Dm15 in aqueous solution is 537 nm, and mass spectrum (EI-MS)m/z (−): 445.0 ([M-2H]$^{2-}$/2), 991.0 ([M-H]$^{-1}$); and the most abundant accurate molecular weight M of the dye (based on free sulfonic acid form) is 991.9.

Based on free sulfonic acid form, Dm16, Dm17 or Dm18 with molecular weight of 1078 are mutual isomers; the maximum absorption wavelength of Dm16, Dm17 or Dm18 in aqueous solution is 528 nm, and mass spectrum (EI-MS)m/z (−): 358.6 ([M-3H]$^{3-}$/3), 538.0 ([M-2H]$^{2-}$/2), 1077.0 ([M-H]$^{-1}$); and the most abundant accurate molecular weight M of the dye (based on free sulfonic acid form) is 1077.9.

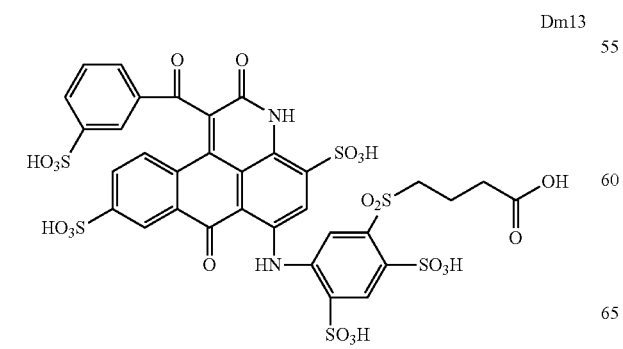

Dm13

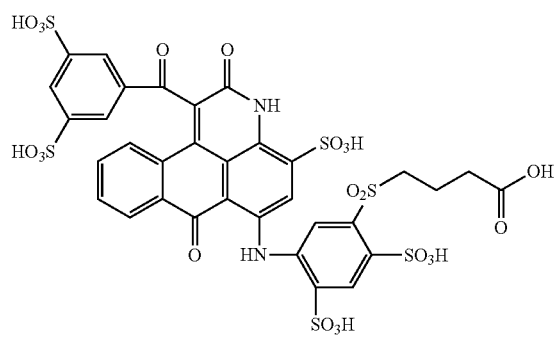

Dm14

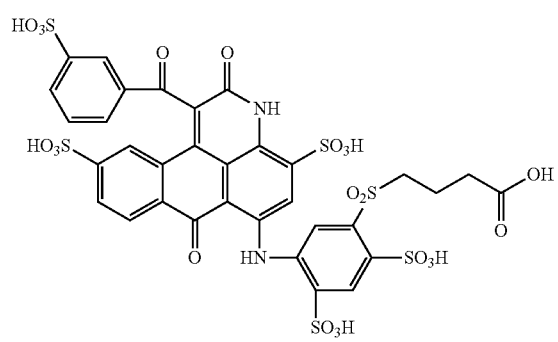

Dm15

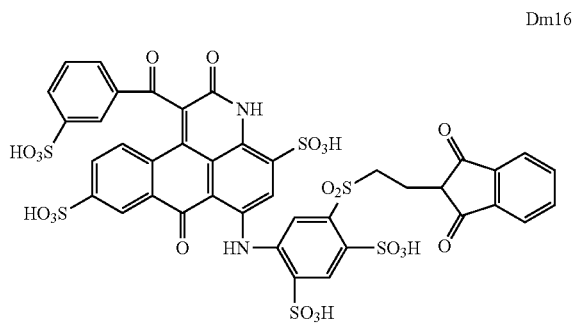

Dm16

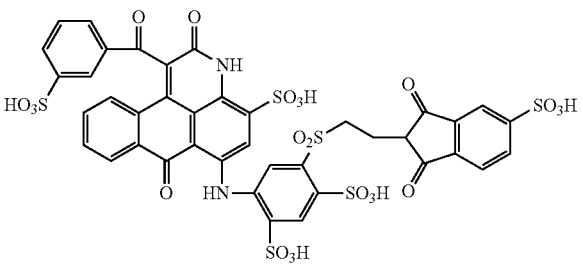

Dm17

Dm18

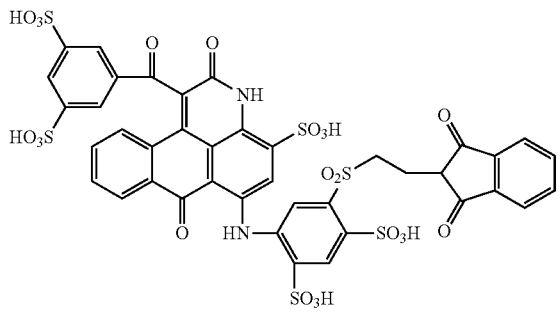

Embodiment 3

The sodium salts of the intermediate V-RB-19' is prepared with IV-RB-19' as a raw material according to the same method as the step 1 in the embodiment 1.

IV-RB-19'

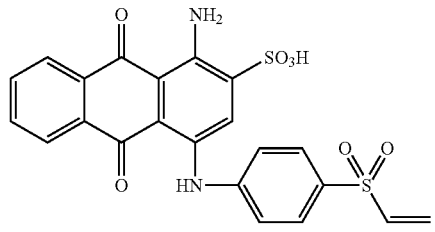

V-RB-19'

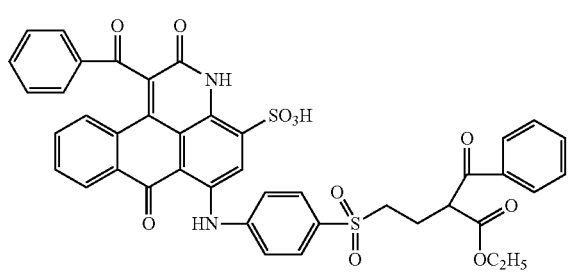

The maximum absorption the of the intermediate V-RB-19' in the form of sodium salts_in water is 543 nm; mass spectrum: m/z(−): 803.2 ([M-H]$^{-1}$). The most abundant precise molecular mass (M) of the intermediate dye product V-RB-19' (calculated by free sulfonic acid) is 804.1.

Then in the sulfonation reaction of the step 2, 550.0 parts of 50% fuming sulfuric acid is added to 675.0 parts of 95.0% sulfuric acid under cooling and stirring to prepare 1225 parts of 10% fuming sulfuric acid, 235 parts of the intermediate dye product V-RB-19' is added at the temperature not higher than 40° C., the reaction temperature is raised to 60-65° C. after addition is finished, and sulfonation reaction is carried out for 5 h. The reaction liquid is added to 2750 parts of crushed ice, then 875 parts of water is added, the reaction liquid is heated to 60° C., insoluble substances are removed by filtering, 850 parts of sodium chloride is added under stirring of 0.5 h and cooling of 2 h to room temperature, and filtering, washing with 1000 parts of 17% sodium chloride solution and drying are carried out to obtain 310 parts of magenta dye. The dye is dissolved in 6000 parts of water, the pH value is adjusted to 8.5, and high-pressure reverse osmosis membrane desalination and concentration are carried out to obtain 3000 parts of solution containing 245 parts of mixed dye (M3, sodium salt), wherein the maximum absorption wavelength in water is 529 nm.

The product mixture is eluted and separated by adopting reversed phase ion pair liquid chromatography according to the same device and manner as the embodiment 1. Pure compounds (sodium salts) of Dp2, Dp4, Dp10 and Dp8 are successively eluted out, and finally a mixture containing little products with low sulfonation degree namely Dp1, Dp3 and Dp7 are finally eluted out.

During high-performance liquid chromatography (HPLC) analysis, according to the same device and manner of the embodiment 1 the compounds in the dye mixture M3 and contents are as follows: Dp2 (30.0%), Dp4 (22.5%), Dp8 (13.0%) and Dp10 (26.0%)

Dp2: yield is 68.5 g; the maximum absorption wavelength in aqueous solution is 537 nm, and mass spectrum (EI-MS) m/z(−): 227.1 ([M-4H]$^{4-}$/4), 303.1 ([M-3H]$^{3-}$/3), 455.0 ([M-2H]$^{2-}$/2), 911.0 ([M-H]$^{-1}$). The most abundant precise molecular mass (M) of dye Dp2 (calculated by free sulfonic acid) is 912.0.

Dp4: yield is 6.2 g; the maximum absorption wavelength in aqueous solution is 528 nm, and mass spectrum (EI-MS) m/z (−): 262.2 ([M-4H]$^{4-}$/4), 349.8 ([M-3H]$^{3-}$/3), 525.1 ([M-2H]$^{2-}$/2), 1051.0 ([M-H]$^{-1}$). The most abundant precise molecular mass (M) of dye Dp4 (calculated by free sulfonic acid) is 1052.0.

Dp8: yield is 28.3 g; the maximum absorption wavelength in aqueous solution is 537 nm, and mass spectrum (EI-MS) m/z(−) is as follows: 331.5 ([M-3H]$^{3-}$/3), 498.0 ([M-2H]$^{2-}$/2), 997.0 ([M-H]$^{-1}$). The most abundant precise molecular mass (M) of dye Dp8 (calculated by free sulfonic acid) is 998.0.

Dp10: yield is 60.4 g; the maximum absorption wavelength in aqueous solution is 530 nm, and mass spectrum (EI-MS) m/z(−) is as follows: 248.7 ([M-4H]$^{4-}$/4), 331.6 ([M-3H]$^{3-}$/3), 497.6 ([M-2H]$^{2-}$/2), 996.9 ([M-H]$^{-1}$). The most abundant precise molecular mass (M) of dye Dp10 (calculated by free sulfonic acid) is 998.0.

The other little dye with low sulfonation degree which is finally eluted out comprises:

Based on free sulfonic acid form, the isomer Dp1 with molecular weight of 832 has the maximum absorption wavelength of 535 nm in aqueous solution, and mass spectroscopy (EI-MS)m/z(−) is as follows: 276.5 ([M-3H]$^{3-}$/3), 415.0 ([M-2H]$^{2-}$/2), 831.0 ([M-H]$^{-1}$); and the most abundant accurate molecular weight $\overline{M}$ (based on free sulfonic acid form) is 832.0;

Based on free sulfonic acid form, the isomer Dp3 with molecular weight of 972 has the maximum absorption wavelength of 533 nm in aqueous solution, and mass spectroscopy (EI-MS)m/z(−) is as follows: 242.1 ([M-4H]$^{4-}$/4), 323.0 ([M-3H]$^{3-}$/3), 485.0 ([M-2H]$^{2-}$/2), 971.0 ([M-H]$^{-1}$); and the most abundant accurate molecular weight $\overline{M}$ (based on free sulfonic acid form) is 972.0;

Based on free sulfonic acid form, the Dp7 with molecular weight of 918 has the maximum absorption wavelength of 534 nm in aqueous solution, and mass spectroscopy (EI-MS) m/z(−) is as follows: 228.6 ([M-4H]$^{4-}$/4), 305.1 ([M-3H]$^{3-}$/3), 458.0 ([M-2H]$^{2-}$/2), 917.0 ([M-H]$^{-1}$); and the most abundant accurate molecular weight $\overline{M}$ (based on free sulfonic acid form) is 918.0;

Embodiment 4

(A) Preparation of Inks

The mixture product M1, M2 or M3 and the pure compound obtained by separation according to the embodiments 1-3 are used as the magenta colorant, and the ink composition is prepared according to the formula shown in following table 1, and the magenta aqueous ink composition is obtained by filtering with a 0.45 μm membrane filter, wherein triethanolamine is added to adjust the pH value of the ink composition to 8-10, and deionized water is added to make the total amount reach 100 parts-by-weight (PBW).

At the same time, in the same way, the ink composition as a contrast is prepared by adopting anthracene pyridone sulfonic acid dye free of carbonyl propyl sulfuryl (Dye1), a hydrolysis derivative of commercial dye C.I. reactive red 180 (abbreviated as reactive red 180) and C.I. direct red 227 for comparison.

Dye1

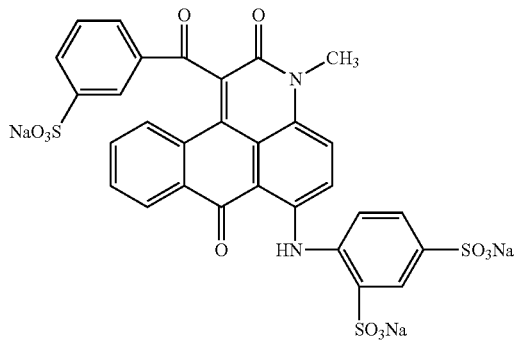

TABLE 1

Compositions of Test Ink

| Compositions | Parts by weight |
| --- | --- |
| Dye | 6 |
| Glycerol | 5 |
| Urea | 5 |
| 2-pyrrolidone | 4 |
| Ethylene glycol monobutyl ether | 2 |
| Isopropanol | 3 |
| Non-ionic surfactant OP-10 | 0.2 |
| Triethanolamine (for adjusting pH) | 0.2 |
| EDTA | 0.1 |
| Fungicide | 0.01 |
| Deionized water | Supplemented to 100 parts by weight |

(B) Ink-Jet Printing

Use an ink-jet printer (Epson 270 manufactured by Epson Company), glossy photo paper (Epson) and the above described ink compositions for ink-jet printing.

(C) Evaluation of Ink-Jet Printed Images (1) Xenon Lamp Light-Resistance Test of the Printed Images Irradiate the printed glossy photo paper manufactured by Canon and Epson with Xenon-lamp Weathering Test Chamber ZG-P (manufactured by China Surui Company) at 60% RH and 24° C. with illuminance of 0.36 W/m² for 50 h to test the color difference ($\Delta E$) before and after the test. The color difference ($\Delta E$) is calculated from the differences of values of L*, a*, b* before and after the test in the above described color measurement system (Unterlab) by the followings formula:

$$\Delta E = ((\text{difference of } L^*)^2 + (\text{difference of } a^*)^2 + (\text{difference of } b^*)^2)^{1/2}.$$

Three grades will be divided for the evaluation based on the following benchmark:
$\Delta E < 10$ ○
$\Delta E < 20$ Δ
$\Delta E > 20$ x (2) Ozone Gas Resistance of the Printed Images Place the printed images in the Ozone Weathering Test Chamber (manufactured by China Surui Company) at 60% RH, 24° C. and 40 ppm ozone. Calculated the color difference ($\Delta E$) before and after the test by the same method as described in (1) above and evaluate it in 3 grades based on the following benchmark:
$\Delta E < 10$ ○
$\Delta E < 20$ Δ
$\Delta E > 20$ x (3) Moisture Resistance of the Printed Images Place the printed images in the Constant Temperature and Humidity Chamber (manufactured by China Surui Company) at 50° C. and 90% RH for 168 h; judge the bleeding of the ink by bare eyes before and after the test and evaluate it in 3 grades based on the following benchmark:
No bleeding ○
Slight bleeding Δ
Notable bleeding x (D) Evaluation of the Dye Solubility in Water (g/100 g Water)
Solubility of the dye in water >30 ○
Solubility of the dye in water >15-20 Δ
Solubility of the dye in water <15 x (E) Evaluation of Long-Term Stability of the Dye in Aqueous Solvent System Heat and dissolve the system of 20 parts of dyes, 70 parts of water and 10 parts of ethylene glycol; after the solution cools down, store it airtight at a constant temperature of 50° C. for 7d; cool it down and store it at 0° C. for 7d; filter the solution and evaluate it in 3 grades based on the following benchmark:
No precipitation ○
Slight precipitation Δ
Notable precipitation x All the test results are listed in Table 2.

TABLE 2

Comparison of Test Performance

| Variety of dyes used | Ultraviolet resistance of ink printed images | Ozone resistance of ink printed images | Water resistance of ink printed images | Solubility of dye in water | Long-term stability of the dye in aqueous solvent system |
| --- | --- | --- | --- | --- | --- |
| M1 | ○ | ○ | ○ | ○ | ○ |
| M2 | ○ | ○ | ○ | ○ | ○ |
| M3 | ○ | ○ | ○ | ○ | ○ |
| Dm1 | ○ | Δ | ○ | ○ | ○ |
| Dm2 | ○ | ○ | ○ | ○ | ○ |
| Dm3 | ○ | ○ | ○ | Δ | ○ |
| Dm4 | ○ | ○ | ○ | ○ | ○ |
| Dm6 | ○ | ○ | ○ | ○ | ○ |
| Dm8 | ○ | ○ | ○ | ○ | ○ |
| Dm10 | ○ | ○ | ○ | ○ | ○ |
| Dp2 | ○ | ○ | ○ | ○ | ○ |
| Dp4 | ○ | ○ | ○ | ○ | ○ |
| Dp8 | ○ | ○ | ○ | ○ | ○ |
| Dp10 | ○ | ○ | ○ | ○ | ○ |
| Dye1 | ○ | ○ | ○ | Δ | ○ |
| C.I. reactive red 180 | x | x | Δ | Δ | Δ |
| C.I. direct red 227 | x | x | Δ | x | Δ |

The comparison shows that anthrapyridone sulfonic acid dyes with carbonyl propyl sulfuryl of the present invention have extremely excellent solubility and long-term stability for use in inkjet inks, and images printed with its inkjet ink compositions have outstanding light resistance, ozone resistance and moisture resistance.

Industrial Applicability

The carbonyl propyl sulfury anthrapyridone sulfonic acid compounds shown in formula (I) and (III) and their mixtures are featured by high solubility and stability in water and luster and brightness suitable for ink-jet printing. As magenta ink compositions prepared with these compounds have outstanding storage stability and images printed with the ink are featured by outstanding light resistance, ozone resistance and moisture resistance, these compounds are magenta dyes suitable for ink-jet printing.

What is claimed is:

1. A class of compounds shown in general formula (I) or (III), salts thereof or their mixtures:

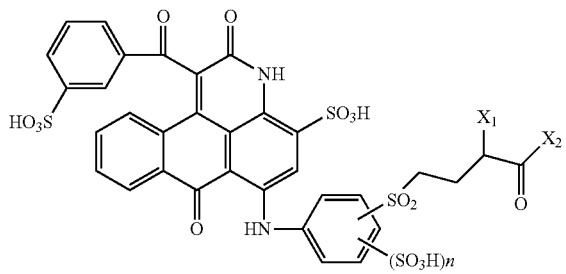

I wherein the general formula (I):
$X_1$ is H or $CO_2H$;
$X_2$ is phenyl group with 0-2 sulfonic acid substituents, and the sulfonic acid substituents are located at random positions of a benzene ring;
n is an integer of 0-2;

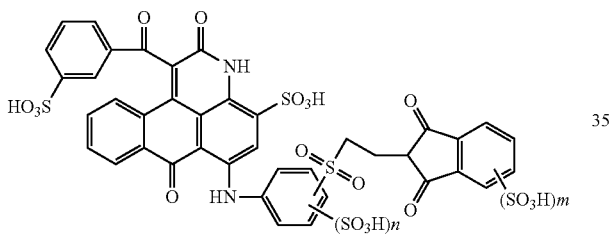

III in the general formula (III), n and m are respectively an integer of 0-2.

2. The compounds, or salts thereof, or their mixtures according to claim 1, wherein n and m are respectively an integer of 1-2.

3. The compounds, or salts thereof, or their mixtures according to claim 1, wherein the salts of the compounds shown in the general formula (I) or (III) are selected from the group consisting of the following cation salts: $Li^+$, $Na^+$, $K^+$, $NH_4^+$, and organic ammonium salt $N^+R_1R_2R_3R_4$, of which $R_1, R_2, R_3, R_4$ are respectively the same or different H, $C_{1-18}$ alkyl group, cyclohexyl group, $CH_2CH_2OH$, $CH(CH_3)CH_2OH$ or benzyl group.

4. A method for preparing the compounds shown in the general formula (I) or (III), the salts thereof or their mixtures according to claim 1, comprising the following steps:

(1) synthesizing an intermediate compound shown in the general formula (V):

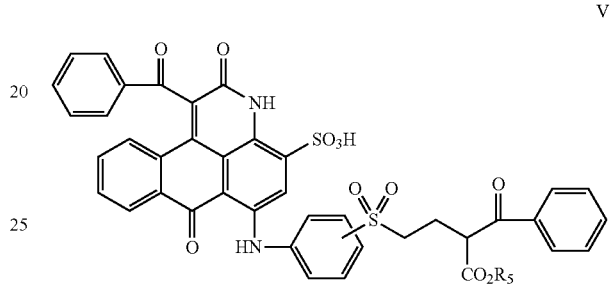

V in the general formula V, $R_5$ is $C_1$-$C_4$ alkyl group; wherein the synthesis steps comprise: based on a compound shown in the general formula (IV) or (IV') as a raw material, carrying out cyclization reaction on the compound shown in the general formula (IV) or (IV') and benzoyl acetic acid ester

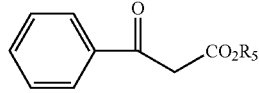

in an organic solvent at the temperature of 100-250° C. for 2-10 h to form the intermediate compound shown in the general formula (V),

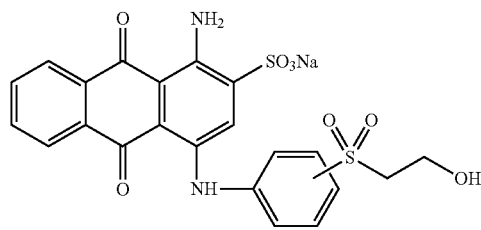

IV or

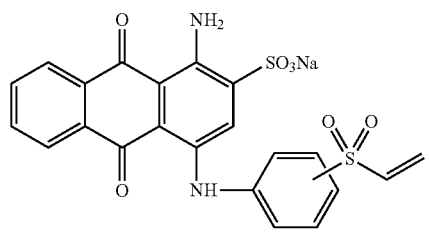

IV'

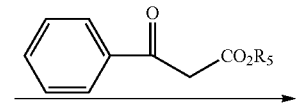

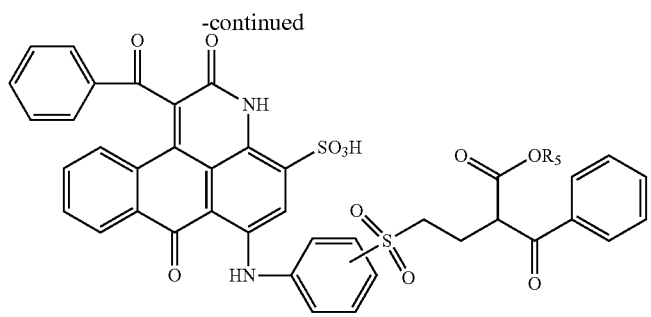

V cool the reaction system after the cyclization and filter the compound of general formula (V) separated out from the liquid reaction system to obtain the solid intermediate (V) compounds;

the aforesaid organic solvent has the boiling point of 100-300° C. and can dissolve or partially dissolve the reaction raw material (IV) or (IV');

(2) sulfonation and decomposition step: the intermediate compound shown in the general formula (V) is sulfonated with fuming sulfuric acid ($SO_3 \cdot H_2SO_4$) containing 5-30% $SO_3$ or chlorosulfonic acid under the temperature of 10-120° C., and simultaneously decomposition reaction occurs for 24 h to generate a mixture, wherein the mixture comprises one or more the compounds shown in the general formula (I) and one or more compounds shown in the general formula (III);

(3) salting-out step: the mixture obtained in the step (2) is salted out with a salt to generate a salt mixture, wherein the salt mixture comprises one or more salts of the compounds shown in the general formula (I), and one or more salts of the compounds shown in the general formula (III);

the salt utilized in the salting-out step is an inorganic salt, and the inorganic salt is selected from the group consisting of ammonium chloride, sodium chloride and lithium chloride;

(4) seperation step: the salts of the compounds shown in the general formula (I) and (III) are separated out from the salt mixture by adopting reversed phase ion-pair chromatography, and the obtained salts of the compounds are respectively desalinated to respectively generate the compounds shown in the general formula (I) and (III).

5. The method according to claim 4, wherein in the step (1), after the cyclization reaction is finished, the reaction system is cooled to 0-50° C.

6. The method according to claim 4, wherein in the step (1), the organic solvents utilized in the cyclization reaction include one or more of the follwing: toluene, dimethylbenzene/isomers of dimethylbenzene/isomer mixture, trimethylbenzene/isomers of trimethylbenzene/isomer mixture, diethylbenzene/isomers of diethylbenzene/isomer mixture, triethylbenzene /isomers of triethylbenzene/isomer mixture, petroleum ether, ethylene glycol dimethyl ether, ethylene glycol diethyl ether, ethylene glycol dipropyl ether, ethylene glycol dibutyl ether, 1,2 -propylene glycol dimethyl ether, 1,2 -propylene glycol diethyl ether, 1,2 -propylene glycol dipropyl ether, 1,2 -propylene glycol dibutyl ether, diethylene glycol dimethyl ether, diethylene glycol diethyl ether, diethylene glycol dipropyl ether, diethylene glycol dibutyl ether, chlorobenzene, dichlorobenzene/isomers of dichlorobenzene/isomer mixture, nitrobenzene,dimethyl sulfoxide (DMSO), dimethyl formamide (DMF), N-methyl pyrrolidone, sulfolane, and mixture of the above solvents.

7. The method according to claim 6, wherein the organic solvent is selected from the group consisting of xylene, diethylbenzene, trimethylbenzene, chlorobenzene, dichlorobenzene, nitrobenzene, DMSO, DMF and a mixture thereof.

8. The method according to claim 4, wherein in the step (1), a sub-step is included: during or after the reaction system cools down, add low-boiling point organic solvents with low solubility of the intermediate (V) and boiling points of 30-150° C. to promote full separation of the intermediate (V);

the low-boiling point organic solvent is selected from the group consisting of methanol, ethanol, propanol, isopropanol, acetone, acetonitrile, petroleum ether, cyclohexane, and their mixtures.

9. The method according to claim 5, wherein in the step (1), a sub-step is included: during or after the reaction system cools down, add low-boiling point organic solvents with low solubility of the intermediate (V) and boiling points of 30-150° C. to promote full separation of the intermediate (V);

the low-boiling point organic solvent is selected from the group consisting of methanol, ethanol, propanol, isopropanol, acetone, acetonitrile, petroleum ether, cyclohexane, and their mixtures.

10. The method according to claim 6, wherein in the step (1), a sub-step is included: during or after the reaction system cools down, add low-boiling point organic solvents with low solubility of the intermediate (V) and boiling points of 30-150° C. to promote full separation of the intermediate (V);

the low-boiling point organic solvent is selected from the group consisting of methanol, ethanol, propanol, isopropanol, acetone, acetonitrile, petroleum ether, cyclohexane, and their mixtures.

11. The method according to claim 4, wherein during the cyclization reaction of the step (1), add alkalis to the cyclization reaction of step (1) to promote the reaction, wherein said alkalis include one or more of the following: sodium carbonate, sodium bicarbonate, potassium carbonate, potassium bicarbonate, lithium carbonate, lithium bicarbonate, ammonium carbonate, ammonium bicarbonate, sodium phosphate, disodium hydrogen phosphate, potassium phosphate, dipotassium hydrogen phosphate, ammonium phosphate, diammonium hydrogen phosphate, lithium phosphate, dilithium hydrogen phosphate, sodium acetate, potassium acetate, lithium acetate, ammonium acetate, sodium oxalate, potassium oxalate, lithium oxalate, ammonium oxalate, sodium hydroxide, potassium hydroxide , aluminum hydroxide or lithium hydroxide, and more preferably sodium carbonate and sodium bicarbonate.

12. The method according to claim 5, wherein during the cyclization reaction of the step (1), add alkalis to the cyclization reaction of step (1) to promote the reaction, wherein said alkalis include one or more of the following; sodium carbonate, sodium bicarbonate, potassium carbonate, potassium bicarbonate, lithium carbonate, lithium bicarbonate, ammonium carbonate, ammonium bicarbonate, sodium phosphate, disodium hydrogen phosphate, potassium phosphate, dipotassium hydrogen phosphate, ammonium phosphate, diammonium hydrogen phosphate, lithium phosphate, dilithium hydrogen phosphate, sodium acetate, potassium acetate, lithium acetate, ammonium acetate, sodium oxalate, potassium oxalate, lithium oxalate, ammonium oxalate, sodium hydroxide, potassium hydroxide , aluminum hydroxide or lithium hydroxide, and more preferably sodium carbonate and sodium bicarbonate.

13. The method according to claim 6, wherein during the cyclization reaction of the step (1), add alkalis to the cyclization reaction of step (1) to promote the reaction, wherein said alkalis include one or more of the following; sodium carbonate, sodium bicarbonate, potassium carbonate, potassium bicarbonate, lithium carbonate, lithium bicarbonate, ammonium carbonate, ammonium bicarbonate, sodium phosphate, disodium hydrogen phosphate, potassium phosphate, dipotassium hydrogen phosphate, ammonium phosphate, diammonium hydrogen phosphate, lithium phosphate, dilithium hydrogen phosphate, sodium acetate, potassium acetate, lithium acetate, ammonium acetate, sodium oxalate, potassium oxalate, lithium oxalate, ammonium oxalate, sodium hydroxide, potassium hydroxide , aluminum hydroxide or lithium hydroxide, and more preferably sodium carbonate and sodium bicarbonate.

14. An ink-jet water-based ink composition, comprising 1-20 wt % of the compounds, the salts thereof or their mixtures according to claim 1, 5-50 wt % of organic solvent miscible with water and 30-94 wt % of water, wherein the sum of the component contents is 100% based on the total weight of the composition;
said water-miscible organic solvents include one or more of the following: ethanol, propanol, isopropanol, ethylene glycol, diethylene glycol, triethylene glycol, glycerol, ethylene glycol monobutyl ether, diethylene glycol monobutyl ether, triethylene glycol monobutyl ether, propylene glycol, butanediol, pentanediol, hexanediol, diglycerol, 2-pyrrolidone and N-methyl -2-pyrrolidone.

15. The ink-jet water-based ink composition according to claim 14, wherein said compounds, or salts thereof, or their mixtures, wherein n and m are respectively an integer of 1-2.

16. The ink-jet water-based ink composition according to claim 14, wherein the salts of the compounds shown in the general formula (I) or (III) are selected from the group consisting of the following cation salts: $Li^+$, $Na^+$, $K^+$, $NH_4^+$, and organic ammonium salt $N^+R_1R_2R_3R_4$, of which $R_1$, $R_2$, $R_3$, $R_4$ are respectively the same or different H, $C_{1-18}$ alkyl group, cyclohexyl group, $CH_2CH_2OH$, $CH(CH_3)CH_2OH$ or benzyl group.

17. An application of the synthesized compounds, the salts thereof or their mixtures according to claim 1, serving as a colorant for the following materials: ink, coating, paint, laser printing toner, marker, fabric, glass, ceramics or polymers.

\* \* \* \* \*

UNITED STATES PATENT AND TRADEMARK OFFICE
CERTIFICATE OF CORRECTION

PATENT NO. : 8,734,580 B2  
APPLICATION NO. : 13/919996  
DATED : May 27, 2014  
INVENTOR(S) : Xiaojun Peng et al.

It is certified that error appears in the above-identified patent and that said Letters Patent is hereby corrected as shown below:

On the Title page, please replace item (72) the fifth Inventors' name from "Licheng Liaoning" to --Licheng WANG--

Signed and Sealed this  
Seventh Day of April, 2015

Michelle K. Lee  
*Director of the United States Patent and Trademark Office*